United States Patent
Zurawski

(10) Patent No.: US 12,292,441 B2
(45) Date of Patent: May 6, 2025

(54) **RECOMBINANT *ACINETOBACTER BAUMANNII* STRAIN AB5075**

(71) Applicant: The Government of The United States, as represented by The Secretary of The Army, Fort Detrick, MD (US)

(72) Inventor: Daniel V Zurawski, New Market, MD (US)

(73) Assignee: The Government of the United States, as Represented by the Secretary of the Army, Fort Detrick, MD (US)

( * ) Notice: Subject to any disclaimer, the term of this patent is extended or adjusted under 35 U.S.C. 154(b) by 229 days.

(21) Appl. No.: 17/191,490

(22) Filed: Mar. 3, 2021

(65) Prior Publication Data
US 2021/0206840 A1   Jul. 8, 2021

Related U.S. Application Data

(62) Division of application No. 15/505,375, filed as application No. PCT/US2015/046221 on Aug. 21, 2015, now Pat. No. 10,961,298.

(60) Provisional application No. 62/040,407, filed on Aug. 21, 2014.

(51) Int. Cl.
| | |
|---|---|
| G01N 33/569 | (2006.01) |
| A61K 39/00 | (2006.01) |
| C07K 16/12 | (2006.01) |
| C12N 1/20 | (2006.01) |

(52) U.S. Cl.
CPC .... *G01N 33/56911* (2013.01); *C07K 16/1203* (2013.01); *C07K 16/1218* (2023.08); *C12N 1/20* (2013.01); *A61K 2039/505* (2013.01); *C07K 2317/21* (2013.01); *C07K 2317/34* (2013.01); *C07K 2317/565* (2013.01); *C07K 2317/70* (2013.01); *G01N 2333/212* (2013.01)

(58) Field of Classification Search
CPC ............ C07K 16/1203; C07K 16/1217; C07K 2317/21; C07K 2317/34; C07K 2317/565; C07K 2317/70; C12N 1/20; G01N 33/56911; G01N 2333/212; A61K 2039/505
See application file for complete search history.

(56) References Cited

U.S. PATENT DOCUMENTS

| | | |
|---|---|---|
| 2009/0104682 A1 | 4/2009 | Kim et al. |
| 2017/0240618 A1 | 8/2017 | Zurawski |

OTHER PUBLICATIONS

Marx et al. (Biotechniques vol. 33, pp. 1062-1067).*
Singh S et al: "A monoclonal antibody against Hcp, the Type Six Secretion System needle, protects mice from Acinetobacter baumanni infection", Abstracts Book, Interscience Conference on Antimicrobial Agents & Chemotherapy (ICAAC), America Society for Microbiology, US, vol. 54, Jan. 1, 2014, pp. 1-314a, XP009502010, ISSN: 0733-6373.
Brent S. Weber et al: "Genomic and Functional Analysis of the Type VI Secretion System in Acinetobacter", PLOS One, vol. 8, No. 1, Jan. 24, 2013, p. e55142, XP055432065.
Bingle et al: "Type VI secretion: a beginner's guide", Current Opinion in Micorbiology, Current Biology Ltd, GB, vol. 11, No. 1, Mar. 4, 2008, pp. 3/8, XP022532967, ISSN: 1369-5274.
Nicole Kapitein et al: "Deadly syringes: type VI secretion system activities in pathogenicity and interbacterial competition", Current Opinion in Microbiology, vol. 16, No. 1, Jan. 2, 2013, pp. 52-58, XP055432076, GB, ISSN 1369-5274.
Partial Supplementary European Search Report for EP 15834606.04, dated Jan. 5, 2018.
Carruthers et al., Acinetobacter baumannii Utilizes a Type VI Secretion System for Bacterial Competition, PLoS One, 2013, vol. 8(3):e59388, PDF file: p. 1-8.
Jacobs et al., AB5075, a Highly Virulent Isolate of Acinetobacter baumannii, as a Model Strain for the Evaluation of Pathogenesis and Antimicrobial Treatments. mBio. May-Jun. 2014, vol. 5(3): e01076-14. PDF fie: p. 1-10.
Bleumink-Pluym et al., Identification of a Functional Type VI Secretion System in Campylobacter Jejuni Conferring Capsule Polysaccharide Sensitive Cytotoxicity, PLoS Pathog. 2013, vol. 9(5):e1003393, PDF file: p. 1-11.
Brianthomasho, Reader Comments: "Acinetobacter baumannii Utilizes a Type VI Secretion System for Bacterial Competition", Dec. 19, 2013, <URL: http://www.plosone.org/annotation/listThread.action?root=76269>.
Genbank_CP001182.1, Acinetobacter baumannii AB0057, complete genome. GenBank, Accession No. CP001182.1. Jan. 30, 2014, https://www.ncbi.nlm.nih.gov/nuccore/213054530?sat=4&satkey=105759432.
Adams et al., Comparative Genome Sequence Analysis of Multidrug-Resistant Acinetobacter, baumannii. J Bacterial. 2008, vol. 190(24), p. 8053-64.
NCBI_NZ_CP008706, Acinetobacter baumannii strain AB5075-UW, complete genome, Accession No. NZ_CP008706. Aug. 19, 2015, <URL: http://www.ncbi.nlm.nih.gov/nuccore/NZ_CP008706>.
Gallagher et al., Resources for Genetic and Genomic Analysis of Emerging Pathogen Acinetobacter baumannii. J Bacterial. 2015, vol. 197(12), p. 2027-35.

(Continued)

*Primary Examiner* — Robert A Zeman
(74) *Attorney, Agent, or Firm* — Timothy H. Van Dyke; Wolter Van Dyke Davis, PLLC

(57) ABSTRACT

In this application is described a mutant Acinobacter *baumannii* strain having a deletion or mutation in its genome. The deletion or mutation interrupts the proper translation of the Hcp protein.

4 Claims, 8 Drawing Sheets
Specification includes a Sequence Listing.

(56) References Cited

OTHER PUBLICATIONS

Skolnick et al., From genes to protein structure and function: novel applications of computational approaches in the genomic era, Trends in Biotechnology, 2000, vol. 18, p. 34-39.

Greenspan et al., Defining epitopes: it's not as easy as it seems, Nature Biotechnology, 1999, vol. 7, p. 936-937.

Giusti et al., Somatic diversification of S107 from an antiphosphocholine to an anti-DNA autoantibody is due to a single base change in its heavy chain variable region, Proceedings of the National Academy of Science, 1987, vol. 84, No. 9, p. 2926-2930).

Winkler et al., Changing the antigen binding specificity by single point putations of an anti-p24 (HIV-1) antibody, J. Immunology, 2000, vol. 265, p. 4505-4514.

Chien et al., Significant structural and functional change of an antigen-binding site by a distant amino acid substitution: proposal of r a structural mechanism, Proceedings of the National Academy of Science, 1989, vol. 86 No. 14, p. 5532-5536.

Caldas et al., Humanization of the anti-CD18 antibody 6.7: an unexpected effect of a framework residue in binding to antigen, Mol. Immunol., 2003, vol. 39, No. 15, p. 941-952.

Casadevall et al., Immunoglobulin isotype influences affinity and specificity, Proceedings of the National Academy of Sciences, 2012, vol. 109, No. 31, p. 12272-12273.

Artuso, Irene, et al. "Genome diversity of domesticated Acinetobacter baumannii ATCC 19606T strains." Microbial Genomics, (2022), vol. 8, No. 1.

Tamang, Migma Dorji, et al. "Interaction of Acinetobacter baumannii 19606 and 1656-2 with Acanthamoeba castellanii." The Journal of Microbiology, (2011), vol. 49: 841-846.

Lucidi, Massimiliano, et al. "New shuttle vectors for gene cloning and expression in multidrug-resistant Acinetobacter species." Antimicrobial agents and chemotherapy, (2018), vol. 62, No. 4: 10-1128.

Luna, Brian M., et al. "Selectable markers for use in genetic manipulation of extensively drug-resistant (XDR) Acinetobacter baumannii HUMC1." Msphere, (2017), vol. 2, No. 2: 10-1128.

Blackwell, Grace A., and Ruth M. Hall. "Mobilisation of a small Acinetobacter plasmid carrying an oriT transfer origin by conjugative RepAci6 plasmids." Plasmid, (2019), vol. 103: 36-44.

Pan, Ping, et al. "Effect of Hcp Iron ion regulation on the interaction between Acinetobacter baumannii With human pulmonary alveolar epithelial cells and biofilm formation." Frontiers in Cellular and Infection Microbiology, (2022), vol. 12: 761604.

Sycz, Gabriela, et al. "Modern Acinetobacter baumannii clinical isolates replicate inside spacious vacuoles and egress from macrophages." PLoS pathogens, (2021), vol. 17, No. 8: e1009802.

* cited by examiner

Type Six Secretion System (T6SS):

Graphical representation of the T6SS in A. baumannii

Figure 2 – Over-expression of Hcp from AB5075
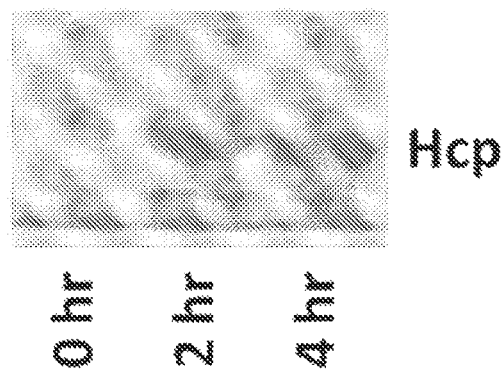

Figure 3. The Tn5::hcp mutant *A. baumannii* is avirulent.

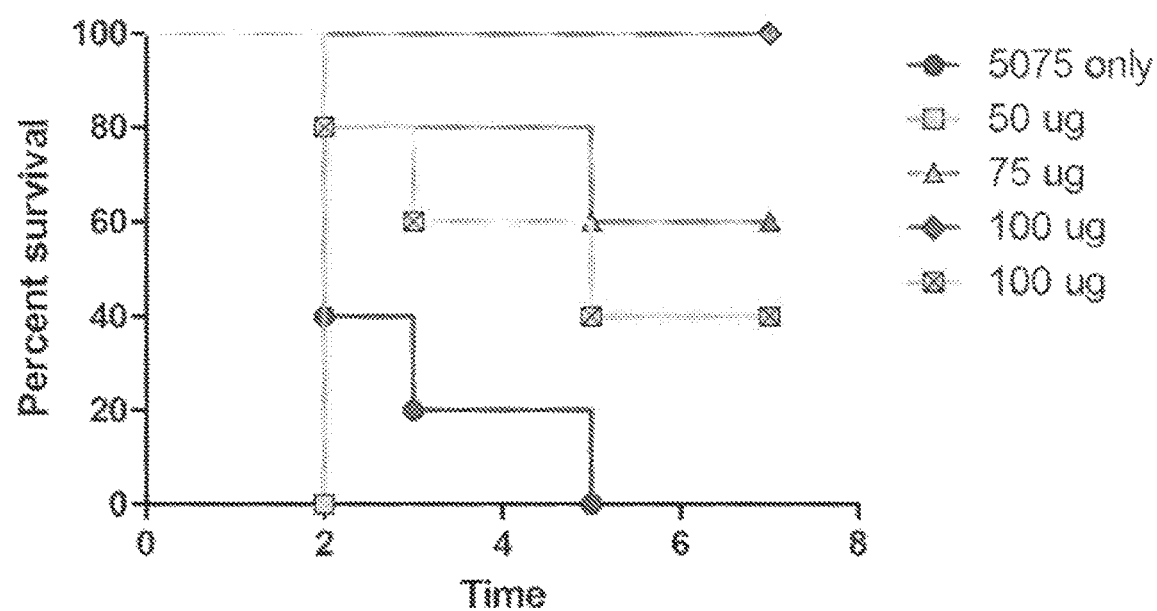
Figure 4. Efficacy of anti-Hcp monoclonal antibody as a therapeutic

Figure 5. Efficacy of the anti-Hcp monoclonal antibody in wound healing.
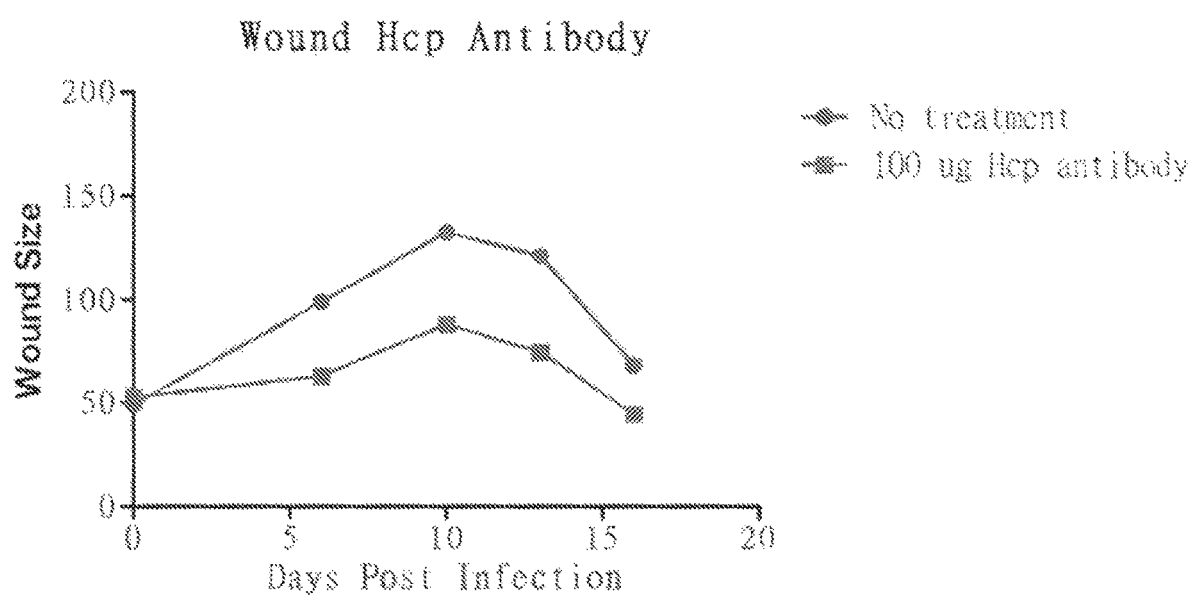

Figure 6. *A. baumannii* titer after treatment with anti-Hcp monoclonal antibody.

Figure 7. Anti-Hcp monoclonal antibody as a diagnostic tool for quantitation of Hcp in human serum.
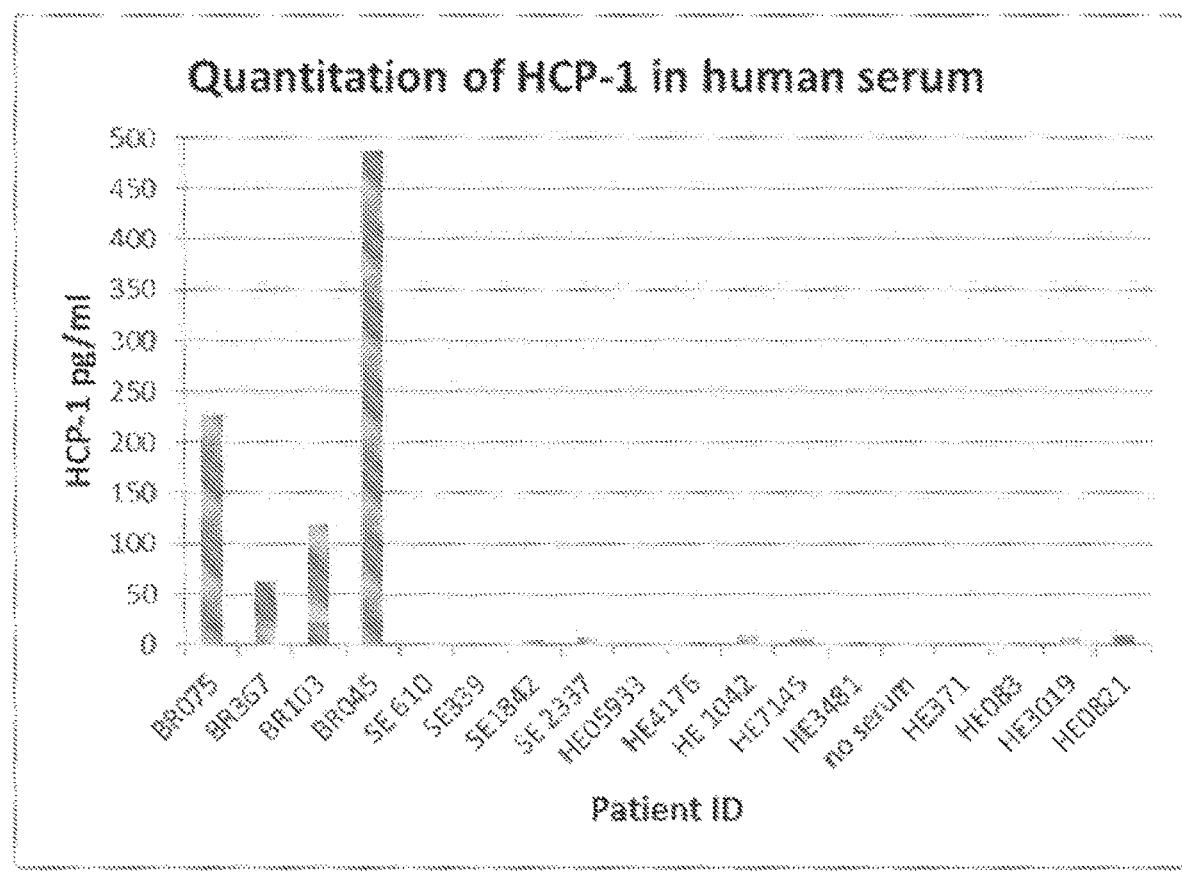

Figure 8. Use of anti-Hcp monoclonal antibody for predicting lethality of *A. baumannii* isolates and monitoring efficacy of antibacterial treatment.

RECOMBINANT *ACINETOBACTER BAUMANNII* STRAIN AB5075

RELATED APPLICATIONS

This application is a division of U.S. application Ser. No. 15/505,375, filed Feb. 21, 2017, which is a National Stage Application under 35 U.S.C. § 371 of International Application No.: PCT/US2015/046221, filed Aug. 21, 2015, which claims priority to U.S. Provisional Application No. 62/040,407, filed Aug. 21, 2014. These applications are incorporated by reference in their entirety.

STATEMENT REGARDING FEDERALLY SPONSORED RESEARCH

This invention was made with government support under Contract No.: W81XWH-08-D-0047 awarded by the United States Army Medical Research and Materiel Command. The U.S. government has certain rights in the invention.

SEQUENCE LISTING

This application incorporates by reference the Sequence Listing which is submitted in electronic computer readable form as a text file entitled, "15505375_SeqList.txt", which was created on Aug. 30, 2017 and is 18544 bytes in size.

BACKGROUND

*Acinetobacter baumannii* is anaerobic, Gram negative, non-motile, non-lactose fermenting, coccobacillus commonly found in food and soil, but now, also frequently in the hospital environment (Bergogne-Berezin and Towner 1996, Clin. Microbiol. Rev. 9, 148-165; Peleg et al., 2008, Clin. Microbiol. Rev. 21, 538-582). While some have questioned the virulence of *A. baumannii*, recent evidence and literature point to more virulent isolates emerging. This bacterial species remains a serious challenge in the ICU with >50% mortality rates with respect to ventilator-associated pneumonia (VAP). *A. baumannii* has also been shown to be the cause of wound and skin and soft tissue infections, osteomyelitis, urinary tract infections, abcess formation, meningitis, and rare cases of aggressive necrotizing faciitus. *A. baumannii* can also grow and disseminate from any infected area of the body and cause septicemia, and these rampant blood infections are a cause of mortality in neonates, pregnant mothers, and other patients who are immunocompromised or susceptible.

The clinical impact of *A. baumannii* infections has grown over the last ten years because of the remarkable ability of the bacterium to acquire and up-regulate antibiotic resistance determinants conferring multi-drug resistance (MDR) (Peleg et al., supra; Karageorgopoulos and Falagas, 2008, Lancet Infect. Dis. 8, 751-762; Gaynes and Edwards, 2005, Clin. Infect. Dis. 41, 848-854). In fact, there are some *A. baumannii* isolates that are resistant to all classes of antibiotics.

The lack of new antibiotics currently being pursued against Acinobacter *baumannii* Gram negative bacteria is of grave concern given the increasing levels of antibiotic resistance. For example, significant carbapenem resistance has developed over the last decade, a jump from about 25% of all isolates to greater than 60%. Also, colistin-resistant *A. baumannii* have emerged leaving the options for treatment extremely limited. Therefore, alternative antibacterial approaches should be considered such as antibodies targeted against the surface-exposed proteins required for virulence and pathogenesis.

SUMMARY OF THE INVENTION

The present invention satisfies the needs described above.

After screening clinical isolates, developing molecular tools to manipulate the genome, and using bioinformatics, the present inventors have discovered that *A. baumannii* has all the components required to have a functional Type Six Secretion System, T6SS, shown to be required for virulence in other Gram negative bacteria. This secretion system secretes into the extracellular milieu but also has translocation machinery, which makes a pore in the host plasma membrane and delivers effector proteins into the host cytoplasm. Once in the host cytoplasm, these translocated proteins are toxins that kill the host cell or disrupt host function, can induce apoptosis of phagocytic immune cells(macrophages/neutrophils), induce invasion, and/or block other aspects of the immune processing and cell signaling (Saier, 2006, J. Membr. Biol. 214, 75-90; Tseng et al., 2009, BMC Microbiol. 9 Suppl 1:82; Bhavsar et al., 2007, Nature 449, 827-834; Coombes et al., 2004, Curr. Biol. 14, R856-867; Pukatzki et al., 2009, supra; Llosa et al., 2009, Mol. Microbiol. 73, 141-151; Ma et al., 2009, Cell Host Microbe 5, 234-243).

Based on sequence data from a clinical isolate AB307-0294 that also causes disease in animal models (Adams et al., 2008, J. Bacteriol. 190, 8053-8064; Russo, et al., 2008, Infect. Immun. 76, 3577-3586) an insertion of about 30 kilobases (kb) of DNA sequence was found which harbors a T6SS. All of the genes encoding the required components (i.e. clpV, hcp, vgrG, etc.) are present in *A. baumannii* genome when compared to what is known about functional T6SS found in *Vibrio cholerae* (*V. cholerae*) and *P. aeruginosa* (Pukatzki et al., 2009, Curr. Opin. Microbiol. 12, 11-17; Shrivastava and Mande, 2008, PLoS One 3, e2955; Bingle et al., 2008, Curr. Opin. Microbiol. 11, 3-8). The T6SS was also present in all of the sequenced *A. baumannii* genomes (including two U.S. Army isolates), and there was a high degree of homology between each strain suggesting that T6SS function is conserved by all *A. baumannii* strains.

The present invention provides a method to disarm the bacteria by attacking the secretion system. Secretion systems are attractive targets for new antibacterial approaches because they disarm the bacteria from harming the host and do not put selective pressure on the bacteria to develop resistance since the bacteria can still replicate (Llosa et al., 2009, supra; Briken, v. 2008, Curr. Drug Targets 9, 150-157; Baron and Coombes, 2007, Infect. Disord. Drug Targets 7, 19-27). The disarmed bacteria, instead, are engulfed by phagocytic, antibacterial cells, such as macrophages and neutrophils, and processed for presentation by the host immune system (Llosa et. al., 2009, supra; Briken 2008, supra; Baron and Coombes, 2007, supra).

A number of strategies have been employed to counteract the secretion systems of Gram negative bacteria. First deletion mutations of the secretion system components have been used for live, attenuated vaccines (Lee and Kessler, 2009, J. Drugs 12, 636-641; Curtiss R. 3$^{rd}$, 2002, J. Clin. Invest. 110, 1061-1066; Venkatesan and Ranallo, 2006, Expert. Rev. Vaccines 5, 669-686; Leibiger et al., 2008, Vaccine 26, 6664-6670). However, vaccination is not an ideal approach for wound infections since vaccinating the whole US military is not cost-effective when only a small proportion are wounded. A more promising strategy involves antibodies that have been generated against secreted components, and when injected into naïve animals (a passive immunization), these antibodies have been shown to protect against a number of bacterial infections, both Gram positive and negative (Kirkpatrick et al., 2006, Vaccine 24, 116-123; Ivanov et al., 2008, Infect. Immun. 76, 5181-5190; Bubeck-Wardenburg and Schneewind, 2008, J. Exp. Med. 205, 287-294; Smith et al., 2009, Infect. Immun. 77, 2730-2740; Cybulski et al., 2009, Mol. Aspects Med. 30, 490-502; Nakouzi et al., 2008, BMC Microbiol. 8, 159). Unlike a vaccine strategy, which relies on a strong antibody titer, once a potent antibody has been acquired, then more can be readily generated and the dosage can be increased to enhance protection (Ivanov et al., 2008, supra; Smith et al., 2009, supra; Nakouzi et al., 2008, supra).

In order to identify targets for antibody protection against *A. baumannii* infection, the antigens required for pathogenesis and virulence had to be identified. To that end, the present inventors identified a clinically relevant *A. baumannii* strain, i.e. AB5075, a strain that causes severe clinical disease in a murine pulmonary model and demonstrates a high level of resistance to most clinically used antibiotics. AB5075 originally isolated from a wounded warrior with osteomyelitis when a bone culture was performed. The strain was amenable to genetic manipulation, allowing the inventors to study and identify virulent factors (Jacobs et al., 2014, mBio 5: 1-10; Gallagher et al., 2015, J. Bacteriol. 197, 2027-2035). Mutant forms of the strain were constructed to verify the target's effect on virulence (Jacobs et al., 2014, supra). In order to test the virulence of the deletion mutant and possible therapies against *A. baumannii* and Gram negative bacteria infection, a novel mouse wound model of *A. baumannii* infection was designed (Mitchell et al., 2014, Antimicrobial Agents and Chemotherapy 58: 1332-1342).

The *Acinetobacter baumannii* strain AB5075 was deposited on 10 Apr. 2024 with the American Type Culture Collection (ATCC) having the address 217 Perry Pkwy, Ste 1, Gaithersburg, MD 20877 under the provisions of the Budapest Treaty under deposit accession number PTA-127747

Using this strategy, three proteins that are required for virulence in animal models were identified on the bacterial surface. These proteins include Hcp, the T6SS needle protein. This protein makes a needle-like structure on the surface of the bacteria and delivers toxins into host cells. The second protein is BauA, a siderophore receptor responsible for bringing iron, an essential element for survival into the bacteria. Lastly, F17 fimbrial protein, now being called FimA2, is responsible for attachment to blood cells and other cells in the body and is required for biofilm formation, another key aspect of survival and antibiotic resistance.

The Hcp gene was cloned, overexpressed, and purified. The purified protein was injected into mice to generate monoclonal antibodies. A monoclonal antibody, 13F7, was produced against Hcp and tested in the novel mouse wound model of *A. baumannii* infection. Hcp monoclonal antibody 13F7 was prophylactically delivered via intraperitoneal injection with increasing doses, and mice were challenged with wild-type AB5075 in a pulmonary model of infection. Dose-dependent protection from infection was observed when 13F7 monoclonal antibody was administered whereas untreated infections killed the majority of mice in just 48 hours. Advantageously, no toxicity was observed with the antibody.

Therefore, it is one object of the present invention to provide a method for prophylactic or therapeutic treatment of *A. baumannii* infection in a mammalian subject, preferably human, comprising administering to the subject an immunologically effective amount of a monoclonal antibody specific for Hcp. In a particular embodiment, the monoclonal antibody is 13F7. In another particular embodiment, the subject is a human. By "prophylactic", it is meant administered before challenge, and by "therapeutic", it is meant administered after challenge.

It is another object of the present invention to provide monoclonal antibodies specific for Hcp. The present invention provides an isolated mouse monoclonal anti-Hcp antibody, 13P7. In another object of the invention is provided an antibody having at least one CDR sequence derived from the herein described mouse anti-Hop 13F7 monoclonal antibody, as well as antibody compositions, glycoforms of the antibody, antibodies with enhanced stability, antibodies with enhanced binding to Hcp, antibodies with enhance affinity to Hcp, bispecific antibodies engineered to express a second distinct binding site or a bispecific T-cell engager, or use of the Fv fragments of any of the antibodies of the present invention in modular IgG construction for bispecific, trispecific or multispecific antibodies. These antibodies and encoding or complementary nucleic acids, vectors, host cells, compositions, formulations, devices, transgenic animals, transgenic plants related thereto, and methods of making and using thereof, as described and enabled herein, in combination with what is known in the art are part of the present invention.

The present invention provides at least one isolated humanized, anti-Hcp momoclonal antibody as described herein. The antibody according to the present invention includes any protein or peptide molecule that comprises at least one complementarity determining region (CDR) of a heavy or light chain or a ligand binding portion thereof, derived from the herein described mouse anti-Hcp monoclonal antibody 13F7, in combination with a heavy chain or light chain constant region, a framework region, or any portion thereof, that can be incorporated into an antibody of the present invention.

In one embodiment, the invention is directed to a human anti-Hcp antibody comprising a light chain and a heavy chain described herein, each of the chains comprising at least part of a human constant region and at least part of a variable region derived from the mouse anti-Hcp 13F7 which has specificity to *A. baumannii* Hcp, said antibody binding with high affinity to Hcp and inhibiting *A. baumannii* infection in vitro and in vivo. The invention also includes fragments or a derivative of such an antibody, such as one or more portions of the antibody chain, such as the heavy chain constant, joining, diversity or variable regions, or the light chain constant, joining or variable regions. The antibodies can be of any class such as IgG, IgM, or IgA or any subclass such as IgG1, IgG2a, IgG4, and other subclasses known in the art. Antibodies useful in the present invention also include human antigen-binding antibody fragments of the antibodies of the present invention including, but are not limited to, Fab, Fab' and F(ab')$_2$, Fd, single-chain Fvs (scFv), single-chain antibodies, disulfide-linked Fvs (sdFv). The invention also includes single-domain antibodies comprising either a VL or VH domain. Further, the antibodies can be produced by any method, such as phage display, or produced in any organism or cell line, including bacteria, insect, mammal or other type of cell or cell line which produces antibodies with desired characteristics, such as humanized antibodies. The antibodies can also be formed by combining a Fab portion and an Fc region from different species, or by keeping the complementarity-determining regions and modifying the framework regions to that of another species.

The antibody can comprise at least one specified portion of at least one complementarity determining region (CDR) (e.g., CDR1, CDR2 or CDR3 of the light chain variable region or heavy chain variable region) derived from the mouse anti-Hcp 13F7 (as such term is defined herein), and/or at least one constant or variable framework region or any portion thereof. The antibody amino acid sequence can further optionally comprise at least one specified substitution, insertion or deletion as described herein or as known in the art.

In one embodiment, the present invention relates to monoclonal antibodies having binding specificity for Hcp. In certain embodiments, the antibodies comprise a light chain variable region specified in SEQ ID NO:1, whose CDR 1, 2 and 3 are defined by amino acid residues SLLNSGNQRNY (SEQ ID NO:2), GAS (SEQ ID NO:3), AND QNDHIYPFTF (SEQ ID NO:4), respectively. In certain embodiments, the antibodies comprise a heavy chain variable region specified in SEQ ID NOs5 whose CDR 1, 2, and 3 are defined by amino acid residues GRIFSSYh (SEQ ID NO:6), IRLKSDNYVT (SEQ ID NO:7), RSYHALDY (SEQ ID NO:8), respectively.

The heavy chain complementary determining regions (or CDRs) include an amino acid sequence at least 90%, 92%, 95%, 97% 98%, 99% or more identical to a sequence selected from the group consisting of SEQ ID NO:6, 7, or 8 and a light chain with CDRs that include an amino acid sequence at least 90%, 92%, 95%, 97% 98%, 99% or more identical to a sequence selected from the group consisting of the amino acid sequence of SEQ ID NO: 2, 3 or 4.

Preferred antibodies of the present invention are those that bind A. buamannii Hcp and inhibit bacterial infection in vitro. Preferred methods for determining monoclonal antibody specificity and affinity by competitive inhibition can be found in Harlow, et al, Antibodies: A Laboratory Manual, Cold Spring Harbor Laboratory Press, Cold Spring Harbor, N.Y., 1988), hereby incorporated by reference thereto. At least one antibody of the invention binds at least one specified epitope specific to A. baumannii Hcp, subunit, fragment, portion or any combination thereof. The epitope can comprise at least one antibody binding region, which epitope is preferably comprised of at least 1-5 amino acid residues of at least one portion of Hcp. In one preferred embodiment, the epitope comprises peptide MKDIYVEFRGKYKVD (SEQ ID NO:9) of Hop.

Another embodiment of the invention relates to antibodies that are functionally equivalent to the antibodies listed above. These functionally equivalent antibodies substantially share at least one major functional property with an antibody listed above and herein described comprising: binding specificity to Hcp antigen, protection against A. baumannii challenge when administered prophylactically or therapeutically, competition for same binding site on the Hop antigen, and/or use of the same combination of complementarity determining regions. Additionally, antibodies included comprise recombinant antibody molecules wherein the variable light chain is essentially SEQ ID No:1, and a variable heavy chain is SEQ ID No:5.

Also contemplated herein is a diagnostic/detection or therapeutic immunoconjugate comprising an antibody component that comprises any of the anti-Hcp antibodies or fragments thereof of the present invention, or an antibody fusion protein or fragment thereof that comprises any of the anti-Hcp antibodies or fragments thereof of the present invention, wherein the antibody component is bound to at least one diagnostic/detection agent or at least one therapeutic agent.

Also contemplated herein is a therapeutic immunoconjugate comprising a therapeutic agent that is selected from the group consisting of an antibiotic, a radionuclide, boron, gadolinium or uranium atoms, an immunomodulator, such as a cytokine, a stem cell growth factor, a lymphotoxin, such as tumor necrosis factor (TNF), a hematopoietic factor such as an interleukin (IL), a colony stimulating factor (CSF) such as granulocyte-colony stimulating factor (G-CSF) or granulocyte macrophage-colony stimulating factor (GM-CSF)), an interferon (IFN) such as interferons-alpha, -beta or -gamma, and a stem cell growth factor, a hematopoietic factor, erythropoietin, thrombopoietin, an antibody specific for Hcp or another antigen of A. baumannii or an antibody for another desired antigen or protein, a hormone, a hormone antagonist, an enzyme, an enzyme inhibitor, a photoactive therapeutic agent, and a combination thereof.

The present invention provides, in one aspect, isolated nucleic acid molecules comprising, complementary, or hybridizing to, a polynucleotide encoding the aforementioned specific anti-Hcp antibodies, comprising at least one specified sequence, domain, portion or variant thereof. In a more specific aspect, the present invention provides nucleotide sequences encoding antibodies of the present invention wherein, wherein the anti-Hcp light chain variable is encoded by the nucleic acid sequence specified in SEQ ID NO:10, and the anti-Hcp heavy chain is encoded by the nucleic acid specified SEQ ID NO:11.

The present invention further provides recombinant vectors comprising said anti-Hcp antibody nucleic acid molecules, host cells containing such nucleic acids and/or recombinant vectors, as well as methods of making and/or using such antibody nucleic acids, vectors and/or host cells. Thus, the invention comprises isolated nucleic acids encoding at least one isolated mammalian anti-Hcp antibody or fragment thereof; an isolated nucleic acid vector comprising the isolated nucleic acid, and/or a prokaryotic or eukaryotic host cell comprising the isolated nucleic acid. The host cell can optionally be at least one selected from COS-1, COS-7, HEK293, BHK21, CHO, BSC-1, Hep G2, 553, SP2/0, 293, HeLa, myeloma, or lymphoma cells, or any derivative, immortalized or transformed cell thereof. Also provided is a method for producing at least one anti-Hcp antibody, comprising translating the antibody encoding nucleic acid under conditions in vitro, in vivo or in situ, such that the antibody is expressed in detectable or recoverable amounts.

The present invention also provides at least one method for expressing at least one aforementioned anti-Hcp antibody in a host cell, comprising culturing a host cell as described herein under conditions wherein at least one anti-Hcp antibody is expressed in detectable and/or recoverable amounts.

The present invention also provides at least one composition comprising (a) an isolated anti-Hcp antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition. In some of these compositions, the antibodies are conjugated to a cytotoxic agent (i.e., an agent that impairs the viability and/or the functions of a bacteria) such as an antibiotic, a toxin, or a radionuclide.

The present invention further provides at least one anti-Hcp antibody method or composition, for administering a therapeutically effective amount to modulate or treat at least one A. baumannii bacterial infection in a cell, tissue, organ, animal or patient and/or, prior to, subsequent to, or during a related condition, as known in the art and/or as described herein. Since Hcp is a conserved target and is found in almost every strain of *A. baumannii*, it is expected that the anti-Hcp antibody described herein will be useful for treatment of infection by different strains of *A. baumannii* with a T6SS needle protein Hcp.

A further embodiment of the present invention provides for mixtures of the above-described antibodies, as well as to methods of using individual antibodies, or mixtures thereof for the prevention and/or therapeutic treatment of *A. baumannii* infections and/or Gram negative bacterial infections in vitro and in vivo, or alleviating a symptom associated with such pathologies. Pharmaceutical compositions according to the invention can include one or more antibody of the invention and one or more carrier. These pharmaceutical compositions can be included in kits.

Thus, the invention provides a method for treating an *A. baumannii* or Gram negative bacteria related condition in a cell, tissue, organ or animal, comprising contacting or administering a composition comprising an effective amount of at least one isolated anti-Hcp antibody or fragment thereof of the invention with, or to, the cell, tissue, organ or animal.

Also provided is a medical device, comprising at least one isolated mammalian anti-Hop antibody of the invention, wherein the device is suitable to contacting or administering the at least one anti-Hcp antibody by at least one mode selected from parenteral, subcutaneous, topical, intramuscular, intravenous, intrarticular, intrabronchial, intraabdominal, intracapsular, intracartilaginous, intracavitary, intracelial, intracerebellar, intracerebroventricular, intrathecal, intra-Ommaya, intravitreous, intraocular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

In a further aspect, the disclosure provides a kit comprising at least one anti-Hcp antibody or fragment of the disclosure in lyophilized form in a first container, and an optional second container comprising a diluent or a physiologically acceptable buffer. In one aspect, the disclosure provides a method of treating at least one Hcp mediated condition, comprising administering to a patient in need thereof a formulation provided in a kit and reconstituted prior to administration.

Also provided is an article of manufacture for human pharmaceutical or diagnostic use, comprising packaging material and a container comprising a solution or a lyophilized form of at least one isolated anti-Hcp antibody of the present invention. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracerebellar, intracerebroventricular, intrathecal, intra-Ommaya, intravitreous, intraocular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

A further embodiment provides passive vaccines for treating or preventing Gram negative bacterial infections, and more specifically *A. baumannii* bacterial infections, comprising a therapeutically or prophylactically effective amount of the antibodies of the present invention which protect against Gram negative bacterial infections or *A. baumannii* infections, in combination with a pharmaceutically acceptable carrier or excipient.

In another embodiment, there are provided anti-idiotypic antibodies raised against one of the present monoclonal antibodies for use as a vaccine to elicit an active anti-Hcp antigen response.

In a further embodiment, there are provided antigenic epitopes as a component of a Gram negative bacterial vaccine. For example, the epitopes on Hop recognized by the anti-Hcp antibody of the present invention, or conservative changes of said epitopes which are still recognized by the antibodies, are useful for actively immunizing a host to elicit production of protective antibodies against Gram negative bacteria.

It is another object of the invention to provide a method and test kits for detection of *A. baumannii* infections and/or Gram negative infections, and/or T6SS related infections by detecting the presence of Hop in a sample from a subject suspected of having such an infection. Since Hop is a conserved target and is found in the majority of *A. baumannii* strains, it is expected that the anti-Hcp monoclonal antibody of the present invention and/or fragments thereof described herein will be useful for detection of the majority of *A. baumannii* strains. The method comprises detecting the presence or absence of a complex formed between anti-Hcp antibodies and Hcp in the sample, such that presence or absence of the immunological complex(es) correlates with presence or absence of the respective infection. The anti-Hcp antibodies can be directly or indirectly attached to a suitable reporter molecule, e.g., an enzyme, a radionuclide, or a fluorophore. The test kit includes a container holding one or more anti-Hcp antibodies according to the present invention and instructions for using the antibodies for the purpose of detecting Hcp in a sample.

It is another object of the present invention to provide an *A. baumannii* wherein the Hcp function has been altered, reduced or eliminated. Herein described is a method for introducing Hcp-specific genomic mutations in *A. baumannii* that reduce or eliminate Hcp expression or function. The Hcp mutant is 100% attenuated. Such *A. baumannii* strains are useful as a vaccine, and as a diagnostic tool for testing putative virulence factors and for determining effectiveness of antimicrobials.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

These and other features, aspects, and advantages of the present invention will become better understood with reference to the following description and appended claims, and accompanying drawings where:

FIG. 2. Over-expression of Hop from AB5075. Hcp was PCR amplified from AB5075 with restriction sites at each end. Then, the gene was cloned into the pET22b vector (Novagen, Germany). After confirming a successful cloning, the protein was overexpressed in E. coli with the addition of IPTG. After 2 and 4 hours (hr), samples were taken to confirm expression. At the 4 hr time point, the sample was lysed and purified using a nickel affinity column. The purified Hcp protein was then used to immunize mice for the generation of monoclonal antibodies.

FIG. 3. The Tn5::hcp mutant is avirulent. BALB/c mice received an intraperitoneal (IP) injection on Day −1, prophylactically, of 25 μg of 13F7 anti-Hcp monoclonal antibody (aHcp) diluted in sterile saline (circle and square) or of sterile saline alone (triangle). Mice were inoculated with $5.0 \times 10^6$ colony forming units (CFU) of wild-type AB5075 (square or triangle) or the Tn5::hcp mutant (AB06795—tnab1_kr130913p01q167) (circle) on Day 0. This data is representative of an experiment repeated twice (each group=10 mice total). The difference between the mutant and wild-type infected cells is statistically significant by log-rank (Mantel-Cox) test (P=0.0001).

FIG. 4. Efficacy of anti-Hcp monoclonal antibody as a therapeutic. Mice were inoculated with $3.0 \times 10^0$ C. FU of wild-type AB5075. 13F7 αHcp was dosed as follows: Circle: no αHcp treatment, negative control—no protection. Square: One dose αHcp—Day −1: 50 μg=no protection. Triangle: Two doses αHcp—Day −1: 50 μg, Day 1: 25 μg (75 μg total)=60% survival. Diamond: Three doses—Day −1: 50 μg, Day 1: 25 μg, Day 3: 25 μg (100 μg total)=100% survival. Square w/X: One dose—Day −1: 100 μg=40% survival.

FIG. 5. Efficacy of the anti-Hop monoclonal antibody in wound healing. Using the murine wound model, mice were injected IP with 100 μg αHcp (squares) or sterile saline (circles) on Day −1. Balb/C mice were then inoculated on Day 0 with AB5075, $5.0 \times 10^4$ CFU. Wound size was measured every three days over the course of 18 days. αHcp antibody treatment enhanced wound healing as wound size was reduced at day 6, 10, 12, and 15.

FIG. 6. A. baumannii titer after treatment with anti-Hcp monoclonal antibody. Using the murine wound model, mice were injected IP with 100 μg αHcp (squares) or sterile saline (circles) on Day −1. Balb/C mice were then inoculated on Day 0 with AB5075, $5.0 \times 10^4$ CFU. After three days, the CFU of the wound bed was measured in mice treated with 100 μg of αHcp (squares) or mice treated with just sterile saline (circles). Only a slight reduction in CFU was observed (about 0.5 $\log_{10}$); however, we believe the bacteria that are present are disarmed as the antibody, which binds to the amino terminus of the protein may prevent proper assembly into the functional, predicted hexamer structure.

FIG. 7. Use of anti-Hcp monoclonal antibody as a diagnostic tool. Serum was isolated from de-identified human patients that were infected with Acinetobacter baumannii (BR075, BR367, BR103, BR045), Staphylococcus epidermidis (SE610, SE339, SE1842, SE2337), or healthy, non-infected patients (HE05933, HE4176, HE7145, HE3481, HE371, HE083, HE3019, HE0821). The 13F7 αHcp antibody was used in an ELISA assay to capture Hcp protein from serum. Only patients infected with Acinetobacter baumannii had Hcp in their blood and serum.

FIG. 8. Use of anti-Hcp monoclonal antibody for predicting lethality of A. baumannii isolate and monitoring efficacy of antibacterial treatment. Blood was collected from two de-identified human patients (P1 and P2) at varying times (1-4) over the course of a two week Acinetobacter baumannii infection. Both patients received antibiotics as treatment. Patient P1 recovered, but Patient P2 did not recover, succumbed to the infection and passed away. The 13F7 αHcp antibody was used in an ELISA assay to capture Hcp protein from blood. Patient P2 signal increased over time before death, while Patient P1's signal reduced over time. This suggests that an αHcp antibody can be used as a diagnostic to predict the intensity and the potential lethality of an Acinetobacter infection.

DETAILED DESCRIPTION

Figure 1:
FIG. 1. Graphical representation of the T6SS in *A. baumannii*. Locations of the T6SS and other genes in the genomic sequence of *A. baumannii* are shown for AB5075 strain. The complete genomic sequence of AB5075 has been deposited in GenBank at accession no. N2_CP008706 with the Hcp gene identified as ABUW_2578. The 167 amino acid sequence of Hcp was deposited in GenBank at WP-000653195.1 and is represented in SEQ ID NO:7.

In the description that follows, a number of terms used in recombinant DNA, microbiology and immunology are extensively utilized. In order to provide a clearer and consistent understanding of the specification and claims, including the scope to be given such terms, the following definitions are provided.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

It also is specifically understood that any numerical value recited herein includes all values from the lower value to the upper value, i.e., all possible combinations of numerical values between the lowest value and the highest value enumerated are to be considered to be expressly stated in this application. For example, if a range is stated as 1% to 50%, it is intended that values such as 2% to 40%, 10% to 30%, or 1% to 3%, etc., are expressly enumerated in this specification.

"Contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or polysaccharide or an epitope on a particular polypeptide or polysaccharide is one that binds to that particular polypeptide or polysaccharide or epitope on a particular polypeptide or polysaccharide without substantially binding to any other polypeptide or polypeptide epitope.

Polyclonal antibodies are immunoglobulin molecules that react against a specific antigen, each antibody identifying a different epitope on the antigen. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Monoclonal antibodies are immunoglobulin molecules that recognize a specific epitope on a specific antigen. Monoclonal antibodies may be prepared using hybridoma methods, such as those described by Kohler and Milstein, Nature, 256:495 (1975). Other methods of preparing monoclonal antibodies are well known in the art. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the polypeptide or polysaccharide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, 1984, J. Immunol., 133:3001; Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the desired antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, 1980, Anal. Biochem., 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., 1995, Protein Eng. 8(10): 1057-1062); single-chain antibody molecules; and multispecific antibodies formed from antibody fragments.

"Nucleic acid," "oligonucleotide," and "polynucleotide" refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. one of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

As used herein, the term "subject" refers to humans, and other animals. Thus, veterinary treatment is provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses (including race horses), poultry, and the like.

The language "biological sample" is intended to include biological material, e.g. cells, blood, tissues, biological fluid, or a solution for administering to a subject, such as a vaccine, or immunoglobulin. By "environmental sample" is meant a sample such as soil and water. Food samples include canned goods, meats, milk, and other suspected contaminated food. Forensic sample includes any sample from a suspected terrorist attack, including paper, powder, envelope, container, hair, fibers, and others.

"Dry" in the context of freeze drying or lyophilization, refers to residual moisture content less than about 10%. Dried compositions are commonly dried to residual moistures of 5% or less, or between about 3% and 0.1%.

Lyophilization (or freeze-drying) is a dehydration technique in which the sample solution (e.g., an antibody composition) is frozen and the solvent (e.g., water or buffer) is removed by sublimation by applying high vacuum. The technique of lyophilization is well known to one of skill in the art (Rey and May, 1999).

"Excipients" or "protectants" (including cryoprotectants and lyoprotectants) generally refer to compounds or materials that are added to ensure or increase the stability of the therapeutic agent during the dehydration processes, e.g. foam drying, spray drying, freeze drying, etc., and afterwards, for long term stability.

A "stable" formulation or composition is one in which the biologically active material therein essentially retains its physical stability and/or chemical stability and/or biological activity upon storage. Stability can be measured at a selected temperature for a selected time period. Trend analysis can be used to estimate an expected shelf life before a material has actually been in storage for that time period.

"Pharmaceutically acceptable" refers to those active agents, salts, and excipients which are, within the scope of sound medical judgment, suitable for use in contact with the tissues or humans and lower animals without undue toxicity, irritation, allergic response and the like, commensurate with a reasonable benefit/risk ratio, and effective for their intended use.

A variety of methods exist in the art for the production of monoclonal antibodies. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). Once isolated, the DNA may be placed into expression vectors, which are then transformed into host cells such as NS0 cells, Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains of a desired species in place of the homologous human sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The term "epitope" is art-recognized. It is generally understood by those of skill in the art to refer to the region of an antigen or antigens that interacts with an antibody. An epitope of a peptide or protein antigen can be linear or conformational, or can be formed by contiguous or noncontinguous amino acid sequences of the antigen. The Hcp antigen, like many proteins, contain many epitopes. The epitopes or peptides recognized by the antibodies of the present invention and conservative substitutions of these peptides which are still recognized by the antibody are an embodiment of the present invention. These peptides offer a convenient method for eluting Hcp to mAb on immunoaffinity columns. For example, when an antibody which recognizes the epitope for 13F7 is used in an immunoaffinity column to purify Hcp antigen, the peptide recognized by the antibody can be added to the immunoaffinity column to elute the Hcp antigen. Further truncation of these epitopes may be possible since antigenic epitopes have been reported to be represented by as few as five amino acid residues.

The nucleotide and amino acid sequence of the heavy and light chain variable regions and the CDR domains of the mAbs of the invention are described in this application. The invention further provides polynucleotides comprising a nucleotide sequence encoding any number of CDR domains of the invention and fragments thereof still capable of binding Hcp. The invention also encompasses polynucleotides that hybridize under stringent or lower stringency hybridization conditions to polynucleotides that encode the heavy or light chain variable region or CDR domains of the antibody of the present invention.

The polynucleotides may now be obtained by any method known in the art. For example, a polynucleotide may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Since the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties), to generate antibodies having a different amino acid sequence, for example to create amino acid substitutions, deletions, and/or insertions.

A vector comprising any of the above-described isolated or purified nucleic acid molecules, or fragments thereof, is further provided by the present invention. Any of the above nucleic acid molecules, or fragments thereof, can be cloned into any suitable vector and can be used to transform or transfect any suitable host. The selection of vectors and methods to construct them are commonly known to persons of ordinary skill in the art and are described in general technical references (see, in general, "Recombinant DNA Part D," Methods in Enzymology, Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid sequence as described above or a portion thereof ligated to a replication system functional in a prokaryotic or eukaryotic host cell. Replication systems can be derived from ColE1, plasmid, phage, SV40, bovine papilloma virus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. For example, a cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as 1GT10, IGT11, 1ZapII (Stratagene), IEMBL4, and 1NM1149, also can be used. Examples of plant expression vectors include pBI110, pBI101.2, pBI101.3, pBI121 and pBIN19 (Clontech). Examples of animal expression vectors include pEUK-C1, pMAM and pMAMneo (Clontech). The TOPO cloning system (Invitrogen, Carlsbad, Calif.) also can be used in accordance with the manufacturer's recommendations.

An expression vector can comprise a native or nonnative promoter operably linked to an isolated or purified nucleic acid molecule as described above. The selection of promoters, e.g., strong, weak, inducible, tissue-specific and developmental-specific, is within the skill in the art. Similarly, the combining of a nucleic acid molecule, or fragment thereof, as described above with a promoter is also within the skill in the art.

Suitable viral vectors include, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989); and Ausubel et al., Current Protocols in Molecular Biology, Greene Publishing Associates and John Wiley & Sons, New York, N.Y. (1994).

A retroviral vector is derived from a retrovirus. Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

Optionally, the isolated or purified nucleic acid molecule, or fragment thereof, upon linkage with another nucleic acid molecule, can encode a fusion protein. The generation of fusion proteins is within the ordinary skill in the art and can involve the use of restriction enzyme or recombinational cloning techniques (see, e.g., Gateway.™. (Invitrogen)). See, also, U.S. Pat. No. 5,314,995.

In view of the foregoing, the present invention also provides a composition comprising an above-described isolated or purified nucleic acid molecule, optionally in the form of a vector. The composition can comprise other components as described further herein.

Also in view of the above, the present invention provides a host cell comprising an above-described isolated or purified nucleic acid molecule, optionally in the form of a vector. It is most preferable that the cell of the present invention expresses the vector, such that the oligonucleotide, or fragment thereof, is both transcribed and translated efficiently by the cell. Examples of cells include, but are not limited to, a human cell, a human cell line, E. coli (e.g., E. coli TB-1, TG-2, DH5α, XL-Blue MRF' (Stratagene), SA2821 and Y1090), B. subtilis, P. aerugenosa, S. cerevisiae, N. crassa, insect cells (e.g., Sf9, Ea4) and others set forth herein below. The host cell can be present in a host, which can be an animal, such as a mammal, in particular a human.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain CDR domains represented in SEQ ID NOS: 6, 7, 8, and the light chain CDR molecules represented in SEQ ID NOS: 2, 3, 4 as well as antibody molecules formed by combinations comprising the heavy chain immunoglobulin molecules with light chain immunoglobulin molecules, such as kappa light chain immunoglobulin molecules, and vice versa, as well as fragments and analogs thereof.

In a specific embodiment, the amino acid sequence of the heavy and/or light chain variable domains may be inspected to identify the sequences of the CDRs by well known methods, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. One or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

Fully human antibodies are described in this application. Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/60433, WO 98/24893, WO 98/16664, WO 96/34096, WO 96/33735, and WO 91/10741; each of which is incorporated herein by reference in its entirety. The techniques of Cole et al., and Boerder et al., are also available for the preparation of human monoclonal antibodies (Cole et al., Monoclonal Antibodies and Cancer Therapy, Alan R. Riss, (1985); and Boerner et al., J. Immunol., 147(1):86-95, (1991)).

Human antibodies produced using other techniques but retaining the variable regions or CDR domains or parts thereof of the mAb of the present invention are part of this invention. Human antibodies can also be produced using transgenic mice which are incapable of expressing functional endogenous mouse immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661, 016; 5,545,806; 5,814,318; 5,886,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Also human mAbs could be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12; 899-903 (1988)).

The antibodies of the present invention may be monospecific, bispecific, trispecific or of greater multispecificity. Multispecific antibodies may be specific for different epitopes of Hcp antigen or may be specific for an antigen as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Bispecific antibodies are monoclonal antibodies that have binding specificities for at least two different antigens. In the present invention, one of the binding specificities may be directed towards Hcp, the other may be for any other *A. baumannii* antigen, Gram negative protein, or for a cell-surface protein, receptor, receptor subunit, tissue-specific antigen, virally derived protein, virally encoded envelope protein, bacterially derived protein, or bacterial surface protein, etc.

Methods for making bispecific antibodies are well known. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655-3659 (1991).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies may be prepared in vitro using known methods in synthetic protein chemistry, including those involving cross-linking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239:1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

Further included in the present invention are antibodies that bind to the same epitope as the antibodies of the present invention. Antibodies which compete with 13F7 are considered to recognize the epitope of the 13F7 anti-Hcp antibody and are considered equivalent to the antibody of the present invention. Assays for determining whether or not an antibody competes with an antibody of the present invention are known to a person with ordinary skill in the art and are described below.

To determine if an antibody can compete for binding to the same epitope as the epitope bound by the antibodies of the present invention including the antibodies produced by the hybridomas deposited with the ATCC, a cross-blocking assay, e.g., a competitive ELISA assay, can be performed. In an exemplary competitive ELISA assay, antigen coated on the wells of a microtiter plate is pre-incubated with or without candidate competing antibody and then the biotin-labeled anti-Hcp antibody of the invention is added. The amount of labeled antibody bound to the antigen in the wells is measured using avidin-peroxidase conjugate and appropriate substrate. The antibody can be labeled with a radioactive or fluorescent label or some other detectable and measurable label. The amount of labeled antibody that bound to the antigen will have an indirect correlation to the ability of the candidate competing antibody (test antibody) to compete for binding to the same epitope, i.e., the greater the affinity of the test antibody for the same epitope, the less labeled antibody will be bound to the antigen-coated wells. A candidate competing antibody is considered an antibody that binds substantially to the same epitope or that competes for binding to the same epitope as an antibody of the invention if the candidate antibody can block binding of the antibody by at least 20%, preferably by at least 20-50%, even more preferably, by at least 50% as compared to the control performed in parallel in the absence of the candidate competing antibody. It will be understood that variations of this assay can be performed to arrive at the same quantitative value.

By further mapping of the binding site of the monoclonal antibodies described in this application other peptides useful as a vaccine or a therapeutic can be predicted. Therefore, in another aspect, this invention relates to a method for identifying protective antigenic epitopes as described in the Examples below. Other methods are known in the art and include a method comprising (i) reacting a monoclonal antibody described in this application to different overlapping fragments encompassing the complete antigen, (ii) identifying a fragment to which the protective antibody binds, (iii) narrowing the region containing sites further by reacting the monoclonal with smaller overlapping fragments encompassing the region identified in (ii), and (iv) choosing peptides to which the antibody binds as possible antigenic epitopes. The peptides can then be assayed for their ability to protect an animal from disease, or to reduce the severity of disease. Peptides defining antigenic protective epitopes can be used in a vaccine, for example.

The epitopes or peptides to which the monoclonal antibodies of the present invention bind can constitute all or part of an eventual active vaccine candidate. An active vaccine or therapeutic candidate might comprise these peptide sequences and others. These might be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective immune responses.

The present invention also pertains to hybridomas producing antibodies which bind to an epitope of Hcp protein or antigen. The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above for a more detailed description of the method of fusion.

The present invention still further pertains to a method for detecting Hcp or T6SS needle protein in a sample suspected of containing A. baumannii, or Gram negative bacteria expressing T6SS needle protein. After checking 33 complete genomes and 1025 draft genomes (taking into account redundancy in the NCBI draft genome data set), it was found that Hcp is present in 82% of A. baumannii strains, indicating that the method of the present invention would detect at least 82% of A. baumannii strains. The method includes contacting the sample with an antibody which binds an epitope of the antigen, allowing the antibody to bind to the antigen to form an immunological complex, detecting the formation of the immunological complex and correlating the presence or absence of the immunological complex with the presence or absence of the antigen in the sample. The sample can be biological, environmental or a food sample.

The language "detecting the formation of the immunological complex" is intended to include discovery of the presence or absence of Hcp antigen in a sample. The presence or absence of Hcp antigen can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988 555-612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a subject infected with a Gram negative bacteria or A. baumannii and a monoclonal antibody of the present invention, are allowed to compete for binding of the antigen. The amount of monoclonal bound is then measured, and a determination is made as to whether the serum contains anti-Hcp antibodies. This competitive ELISA can be used to indicate immunity to known protective epitopes in a vaccinee following vaccination and to identify competing antibodies.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 81:1-40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, organs, biological fluid, or a solution for administering to a subject, such as a vaccine, or immunoglobulin. By "environmental sample" is meant a sample such as soil and water. Food samples include canned goods, meats, and others.

Yet another aspect of the present invention is a kit for detecting Hcp or *A. baumannii* bacteria expressing Hcp, in a biological sample. The kit includes a container holding one or more antibodies which binds an epitope of Hcp and instructions for using the antibody for the purpose of binding to the antigen to form an immunological complex and detecting the formation of the immunological complex such that the presence or absence of the immunological complex correlates with presence or absence of the antigen in the sample. Examples of containers include multiwell plates which allow simultaneous detection of Hcp in multiple samples.

As described in greater detail in the Examples, the present inventors have isolated a monoclonal antibodies which bind to epitopes on Hcp and display in vitro and/or in vivo protective properties. Significantly, the reactivity of the mAbs is applicable against a broad variety of different wild type and laboratory *A. baumannii* strains of different types that express Hcp as determined in vitro using ELISA, western blot, radioimmunoprecipitation; or in vivo against challenge with *A. baumannii*. After checking 33 complete genomes and 1025 draft genomes (taking into account redundancy in the NCBI draft genome data set), it was found that Hcp is present in 82% of *A. baumannii* strains. Some of these strain include for example *Acinetobacter baumannii* 1656-2, *Acinetobacter baumannii* A1, *Acinetobacter baumannii* AB0057, *Acinetobacter baumannii* AB030, *Acinetobacter baumannii* AbO4-mff, *Acinetobacter baumannii* AB307-0294, *Acinetobacter baumannii* AB5075-UW, *Acinetobacter baumannii* AbH120-A2, *Acinetobacter baumannii* AC29, *Acinetobacter baumannii* AC30, *Acinetobacter baumannii* ACICU, *Acinetobacter baumannii* ATCC17978, *Acinetobacter baumannii* AYE, *Acinetobacter baumannii* BJAB07104, *Acinetobacter baumannii* BJAB0715, *Acinetobacter baumannii* BJAB0868, *Acinetobacter baumannii* CIP70.10, *Acinetobacter baumannii* IOMTU433, *Acinetobacter baumannii* MDR-TJ, *Acinetobacter baumannii* MDR-ZJ06, *Acinetobacter baumannii* NCGM237, *Acinetobacter baumannii* PKAB07, *Acinetobacter baumannii* SDF, *Acinetobacter baumannii* TCDC-AB0715, *Acinetobacter baumannii* TYTH-1, *Acinetobacter baumannii* XH386, *Acinetobacter baumannii* ZW85-1. Laboratory strains can be derived from wild type strains and include those which have been adapted, and those derived by site-directed mutagenesis.

Given these results, monoclonal antibodies according to the present invention are suitable both as therapeutic and prophylactic agents for treating or preventing infections in a subject caused by at least 82% of *A. baumannii* strains, in addition to Gram negative bacterial infections wherein Hcp is expressed.

In general, this will comprise administering a therapeutically or prophylactically effective amount of one or more monoclonal antibodies of the present invention to a susceptible subject or one exhibiting infection. Any active form of the antibody can be administered, including Fab and F(ab') fragments. Antibodies of the present invention can be produced in any system, including insect cells, baculovirus expression systems, chickens, rabbits, goats, cows, or plants such as tomato, corn, potato, banana or strawberry. Methods for the production of antibodies in these systems are known to a person with ordinary skill in the art. Preferably, the antibodies used are compatible with the recipient species such that the immune response to the mAbs does not result in clearance of the mAbs before bacteria can be controlled, and the induced immune response to the mAbs in the subject does not induce "serum sickness" in the subject. Preferably, the mAbs administered exhibit some secondary functions such as binding to Fc receptors of the subject.

Treatment of individuals having *A. baumannii* infection or a Gram negative bacterial infection wherein Hcp is expressed may comprise the administration of a therapeutically effective amount of one or more of the above nucleic acid molecules, vectors, host cells, antibodies, fusion proteins, conjugates, and in particular monoclonal antibodies of the present invention with or without antibiotics. The above nucleic acid molecules, vectors, host cells, antibodies, fusion proteins and conjugates can be administered to cells, tissue, organ, or animal by at least one mode selected from parenteral, subcutaneous, intramuscular, intravenous, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrathecal, intra-Ommaya, intravitreous, intraocular, intrasynovial, intrathoracic, intrauterine, intravesical, bolus, vaginal, rectal, buccal, sublingual, intranasal, or transdermal. The method can optionally further comprise administering, prior, concurrently, or after the antibody contacting or administering at least one composition comprising an effective amount of at least one compound or protein or cell selected from at least one of a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, antibody or antibody derived conjugates, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog thereof, a cytotoxic or other anti-cancer agent, an anti-metabolite such as methotrexate, an anti-proliferative agent, a cytokine, interleukin, growth factors, a cytokine antagonist, and an anti-TNFα, white cells, T-cells, LAK cells, TIL cells, natural killer (NK) cells, monocytes, NKT cells, engineered T cells or NK cells or monocytes or granulocytes.

Formulations for administration can include injections, aerosol suspensions, respirable particles, ingestible liquid suspensions or solutions in water or non-aqueous media, or solid capsules, sachets, or tablets, ointments, lotions, creams, gels, drops, suppositories, sprays, powder, droppers, swabs, inhalers, among others known in the art. Methods and apparatus for administering the formulations are well known in the art.

Thickeners, flavorings, diluents, emulsifiers, dispersing aids or binders can be desirable. Some of the compositions potentially can be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, and potassium hydroxide, and organic bases, such as mono-, di-, trialkyl and aryl amines and substituted ethanolamines.

In some embodiments, the co-administered antimicrobial is an antibiotic. In some embodiments, the antibiotic has an intracellular target. In some embodiments, the antibiotic targets aerobically-growing bacteria. In some embodiments, the antibiotic is an aminoglycoside. In some embodiments, the antibiotic is selected from the following: Ample Spectrum Penicillins, Amoxicillin, Ampicillin, Bacampicillin, Carbenicillin Indanyl, Mezlocillin, Piperacillin, Ticarcillin, Penicillins and Beta Lactamase Inhibitors, Amoxicillin-Clavulanic Acid, Ampicillin-Sulbactam, Benzylpenicillin, Cloxacillin, Dicloxacillin, Methicillin, Oxacillin, Penicillin G (Benzathine, Potassium, Procaine), Penicillin V, Piperacillin+Tazobactam, Ticarcillin+Clavulanic Acid, Nafcillin, Cephalosporins, Cefadroxil, Cefazolin, Cephalexin, Cephalothin, Caphapirin, Cephradine, Cefaclor, Cefamandol, Cefonicid, Cefotetan, Cefoxitin, Cefprozil, Ceftmetazole, Cefuroxime, Cefuroxime axetil, Loracarbef, Cefdinir, Ceftibuten, Cefoperazone, Cefixime, Cefotaxime, Cefpodoxime proxetil, Ceftazidime, Ceftizoxime, Ceftriaxone, Cefepime, Macrolides and Lincosamines, Azithromycin, Clarithromycin, Clindamycin, Dirithromycin, Erythromycin, Lincomycin, Troleandomycin, Quinolones and Fluoroquinolones, Cinoxacin, Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Trovafloxacin, Oxolinic acid, Gemifloxacin, Perfloxacin, Carbepenems, Imipenem-Cilastatin, Meropenem, Monobactams, Aztreonam, Aminoglycosides, Amikacin, Gentamicin, Kanamycin, Neomycin, Netilmicin, Streptomycin, Tobramycin, Paromomycin, Glycopeptides, Teicoplanin, Vancomycin, Tetracyclines, Demeclocycline, Doxycycline, Methacycline, Minocycline, Oxytetracycline, Tetracycline, Chlortetracycline, Sulfonamides, Mafenide, Silver Sulfadiazine, Sulfacetamide, Sulfadiazine, Sulfamethoxazole, Sulfasalazine, Sulfisoxazole, Trimethoprim-Sulfamethoxazole, Sulfamethizole, Rifampin, Rifabutin, Rifampin, Rifapentine, Oxazolidonones, Linezolid, Streptogramins, Quinopristin+Dalfopristin, Bacitracin, Chloramphenicol, Colistemetate, Fosfomycin, Isoniazid, Methenamine, Metronidazol. Mupirocin, Nitrofurantoin, Nitrofurazone, Novobiocin, Polymyxin B, Spectinomycin, Trimethoprim, Colistin, Cycloserine, Capreomycin, Ethionamide, Pyrazinamide, Para-aminosalicyclic acid Erythromycin ethylsuccinate+sulfisoxazole and others known in the art.

Antibodies of the present invention can be used or administered as a mixture, for example in equal amounts, or individually, provided in sequence, or administered all at once. Effective dosages and schedules for administering the above nucleic acid molecules, vectors, host cells, antibodies, and fusion proteins can be determined empirically, and making such determinations is within the skill in the art. Those skilled in the art will understand that the dosage that must be administered will vary depending on, for example, the subject, the route of administration, whether a nucleic acid molecule, vector, host cell, antibody, fusion protein or conjugate is being administered, and whether other drugs being administered, not to mention the age, condition, and gender of the human and the extent of disease. Guidance in selecting appropriate doses for antibodies (or fusion proteins comprising same) is found in the literature on therapeutic uses of antibodies, e.g., Handbook of Monoclonal Antibodies, Ferrone et al., eds., Noges Publications, Park Ridge, N.J. (1985), Ch. 22 and pp. 303-357; Smith et al., Antibodies in Human Diagnosis and Therapy, Haber et al., eds., Raven Press, New York (1977), pp. 365-389. Nucleic acids, vectors and host cells should be administered so as to result in comparable levels of production of antibodies or fusion proteins thereof.

In general, it is desirable to provide the recipient with a dosage of antibody which is in the range of from about 1 pg/kg-100 µg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 pg/kg-100 pg/kg, 100 pg/kg-500 pg/kg, 500 pg/kg-1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered.

The antibodies capable of protecting against *A. baumannii* are intended to be provided to recipient subjects in an amount sufficient to effect a reduction in the *A. baumannii* infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable diluents can be sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, mannitol, sucrose, mannose, other sugars, tween 80, or mixtures thereof in an aqueous diluent.

Additional pharmaceutical methods may be employed to control the duration of action. Controlled release preparations may be achieved through the use of polymers to complex or absorb the compounds. The controlled delivery may be exercised by selecting appropriate macromolecules (for example polyesters, polyamino acids, polyvinyl, pyrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly (lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Prior to administration, the compositions of the invention can be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized compositions.

Following administration of a nucleic acid molecule, vector, host cell, antibody, fusion protein or conjugate for treating, inhibiting, or reducing the severity of an *A. baumannii* infection, the efficacy of the therapeutic agent can be assessed in various ways well-known to the skilled practitioner. For instance, one of ordinary skill in the art will understand that an antibody of the invention is efficacious in treating or inhibiting an *A. baumannii* infection in a subject by observing that the antibody reduces bacterial load or prevents a further increase in bacterial load. Bacterial loads can be measured by methods that are known in the art, for example, using polymerase chain reaction assays to detect the presence of *A. baumannii* nucleic acid or antibody assays to detect the presence of *A. baumannii* protein in a sample (e.g., but not limited to, blood) from a subject or patient, or by measuring the level of circulating anti-bacterial antibody levels in the patient.

The nucleic acid molecules, vectors, host cells, antibodies, fusion proteins and/or conjugates of the invention can be administered prophylactically to patients or subjects who are at risk for being exposed to *A. baumannii* or who have been newly exposed to *A. baumannii*. In subjects who have been newly exposed to *A. baumannii* but who have not yet displayed the presence of the bacteria (as measured by PCR or other assays for detecting the bacteria) in blood or other body fluid, efficacious treatment with an antibody of the invention partially or completely inhibits the appearance of the bacteria in the blood or other body fluid.

The nucleic acid molecules, vectors, host cells, antibodies, fusion proteins and/or conjugates of the invention can be combined with other well-known therapies and prophylactic vaccines already in use. Such combinations can generate an additive or a synergistic effect with current treatments. The nucleic acid molecules, vectors, host cells, antibodies and/or conjugates of the invention can be combined with other *A. baumannii* antibodies for other virulence proteins such as bauA and F17, to name a few, in addition to other antibiotics and vaccines. Such therapies can be administered in the manner already in use for the known treatment providing a therapeutic or prophylactic effect.

As described above, the compositions can be administered in a pharmaceutically acceptable carrier and can be delivered to the subject's cells in vivo and/or ex vivo by a variety of mechanisms well-known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well-known in the art. Compositions comprising a nucleic acid, optionally in the form of a vector encoding the antibody or fusion protein comprising same, can be introduced into the cells via any gene transfer mechanism, such as, for example, calcium phosphate mediated gene delivery, electroporation, microinjection or proteoliposomes. The transduced cells then can be infused (e.g., in a pharmaceutically acceptable carrier) or homotopically transplanted back into the subject per standard methods for the cell or tissue type. Standard methods are known for transplantation or infusion of various cells into a subject.

Thus, in view of the above, the present invention provides a method of inhibiting an infection of a human at risk of becoming infected with *A. baumannii*. The method comprises administering to the human an infection-inhibiting amount of an above-described nucleic acid, vector, host cell, antibody or fusion protein, whereupon the infection of the human is inhibited. Preferably, the infection is inhibited to such a degree that the human does not evidence the signs and symptoms of infection.

Also in view of the above, the present invention provides a method of reducing the severity of an infection of a human infected with *A. baumannii*. The method comprises administering to the human a severity of infection-reducing amount of an above-described nucleic acid, vector, host cell, antibody or fusion protein, whereupon the severity of the infection of the human is reduced. Preferably, the reduction in the severity of infection is to such a degree that the human does not evidence the signs and symptoms of infection, or preferably the human does not experience an increase in the severity of disease.

In a similar approach, another therapeutic use of the monoclonal antibodies of the present invention is the active immunization of a patient using an anti-idiotypic antibody raised against one or more of the present monoclonal antibodies. Immunization with an anti-idiotype which mimics the structure of the epitope could elicit an active anti-Hcp response (Linthicum, D. S. and Farid, N. R., Anti-Idiotypes, Receptors, and Molecular Mimicry (1988), pp 1-5 and 285-300).

Active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide, with or without adjuvant, in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used e.g., $NH_2$-acetylation or COOH-terminal amidation, to provide additional means for coupling or fusing the peptide to another protein or peptide molecule or to a support.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

In one aspect, in the kit, the concentration of anti-Hcp antibody or specified portion or variant in the first container is reconstituted to a concentration of about 0.1 mg/ml to about 500 mg/ml with the contents of the second container. In another aspect, the second container further comprises an isotonicity agent. In another aspect, the second container further comprises a physiologically acceptable buffer. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

The contents of all cited references (including literature references, issued patents, published patent applications, and co-pending patent applications) cited throughout this application are hereby expressly incorporated by reference.

The following examples are included to demonstrate preferred embodiments of the invention. It should be appreciated by those of skill in the art that the techniques disclosed in the examples which follow represent techniques discovered by the inventors and thought to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Model Strain

While previous studies attempted to examine the virulence of different clinical *A. baumannii* strains utilizing in vivo model systems (de Breij et al., 2012, PloS One 7, e30673; Eveillard et al., 2010, J. Infect. 60, 154-161), the majority of *A. baumannii* researchers still use two American Type Culture Collection (ATCC) strains, ATCC 19606$^T$ and ATCC 17978, which were isolated more than fifty years ago and are not significantly antibiotic resistant. These strains are certainly more amenable to genetic manipulation than most clinical isolates (Smith et al., 2007, Genes Dev. 21, 601-614; Tomaras et al., 2003, Microbiology 149, 3473-3484), share considerable genome homology (>90%) compared to current *A. baumannii* isolates (Sahl et al., 2011, BMC Genomics 12, 291), but they are not representative of contemporary isolates of this rapidly-evolving pathogen. Some researchers, recognizing that the ATCC isolates were dated, have performed studies with more recent clinical isolates; however, genetic manipulation of such isolates has depended on susceptibility to aminoglycosides (Loehfelm et al., 2008, J. Bacteriol. 190, 1036-1044; Ramirez et al., 2010, J. Clin. Microbiol. 48, 1488-1490; Russo et al., 2008, Infect. Immun. 76, 3577-3586), which is often not found in clinical strains (Vila and Pchon, 2012, Expert Opin. Pharmacother. 13, 2319-2336). Therefore, our goal was to carry out a systematic study of our own contemporary clinical strains isolated from patients in the U.S. military healthcare system to identify a strain that is more representative of current clinical isolates, that is highly virulent in established model infections, and can be genetically manipulated without a potential sacrifice with respect to virulence and antibiotic resistance.

In order to identify potential reference strains, a diverse set of 33 *A. baumannii* isolates was chosen based on genetic, isolation site, and antibiotic resistance differences from more than 200 *A. baumannii* strains isolated between 2004 and 2010 from patients in the U.S. military healthcare system. AB0057, first isolated in 2004 at Walter Reed Army Medical Center, was also included as a comparator because this strain is well characterized, and its genome was previously sequenced (Adams et al., 2008, J. Bacteriol. 290, 8053-8064).

The diversity set of *A. baumannii* isolates was determined via Pulsed-Field Gel Electrophoresis (PFGE) analysis, and a multiplex PCR assay previously developed to identify the International clonal complexes (ICC) (Jacobs et al., 2014, supra). Separately, antibiograms were determined using two different automated bacterial identification systems. The majority of strains were found to be multidrug resistant, typical of current clinical strains (data not shown). The genetic similarity of the strains determined by PFGE ranged from 45 to 100% (data not shown). PFGE types were considered to represent the same clones when their genetic similarity was >80% (van Belkum et al., 2007, Clin. Microbial. Infect. 13:1-46); based on this cut off, the 33 strains represent 19 unique clones. When comparing the genetic relatedness of these 19 clones, it was found that the majority of them clustered into three groups, which generally aligned with the ICC designations determined by multiplex PCR (data not shown (Turton et al., 2007, Clin. Microbiol. Infect. 13, 807-81.5). These data were used to select four representative strains for genome sequencing and evaluation in animal models.

Three of the strains chosen represented each one of the three ICC groups, AB5075 (ICC I), AB5711 (ICC II), and AB4857 (ICC III). The fourth strain, AB5256 was an outlier as the OXA-51 allele from this strain amplified with Group 1 primers (Turton et al., 2007, supra), while the csuE allele did not. The isolates were sequenced (Zurawski et al., 2012, J. Bacteriol. 194, 1619-1620) and compared to previously sequenced *A. baumannii* genomes using the BLAST Score Ratio (BSR) approach (Rasko et al., 2005, BMC Bioinformatics 6, 2). This method compares putative peptides encoded in each genome based on the ratio of BLAST scores to determine if they are conserved (BSR value 20.8), divergent (0.8>BSR>0.4), or unique (BSR<0.4). The majority of the proteomes were similar among strains, meaning they had a BSR>0.4, however, each isolate also had a set of unique proteins (data not shown). These results are similar to what has been found previously with MDR *A. baumannii* clinical isolates (Sahl et al. 2011, supra), suggesting that the strains used in this study are not genetic outliers.

Strains were first tested in a *Galleria mellonella* infection model, as this model is well-established to assess virulence and novel therapeutics for bacterial pathogens, including *A. baumannii* (Desbois and Coote, 2012, Adv. Appl. Microbiol. 78, 25-53; Manepalli et al., 2013, J. Med. Microbiol. 62, 1747-1754). AB5075 was found statistically to be more lethal than AB4857, AB5711, and AB0057 (all P values<0.0125).

Separately, to compare the lethality of AB5075 to more commonly utilized *A. baumannii* model strains, the $LD_{50}$ of AB5075, ATCC 17978, and ATCC 19606$^7$ were determined in *G. mellonella*. The $LD_{50}$ of AB5075 was equal to $1.0\times10^4$ CFU. In contrast, the $LD_{50}$ of ATCC 17978, and ATCC 19606$^T$ were $5.0\times10^9$ and $1.0\times10^8$, respectively.

*A. baumannii* strains were examined in a murine pulmonary model of infection because this model is commonly used to assess bacterial virulence and drug efficacy, and survival can be assessed rapidly after an inoculum is delivered(Eveillard et al., 2010, supra; Manepalli et al., 2013, supra). The animals were immunocompromised with two doses of cyclophosphamide before inoculation, a treatment that allows *A. baumannii* to establish an infection (Eveillard et al., 2010, supra). Mice were inoculated on day 0 with one of the five *A. baumannii* representative strains at a dose of $5.0\times10^6$ CFU and monitored over the course of six days. Consistently, mice infected with AB5075 had a mortality rate of 70% within 48-72 hours, and a six day survival rate of 25% (data not shown). The other four strains tested, AB0057, AB5711, AB5256, and AB4857, were less lethal than AB5075 in this model, with six day survival rates of 65, 80, 80, and 85 percent, respectively.

Our success in establishing A85075 infections in multiple animal models suggests the isolate would be an attractive model strain for studying *A. baumannii* virulence. However, in addition to an ideal model strain being highly virulent in animal models, the ability to genetically manipulate the isolate is vital for the study of *A. baumannii* pathogenicity. Because antibiotic resistance determinants are central to many types of genetic manipulations, such as transposon mutagenesis, the antibiotic sensitivity profile of AB5075 was examined in detail. It was observed that AB5075 is susceptible to tetracycline, doxycycline and related antibiotics and to high levels of erythromycin and hygromycin.

With these known susceptibilities, a method previously developed in *A. baumannii* (Dorsey et al., 2002, Appl. Environ. Microbiol. 68, 6353-6360) was adapted for creating AB5075 isogenic mutants by utilizing the hph gene, encoding hygromycin resistance, from pMQ300 (Kalivoda et al., 2011, Mol. Biotechnol. 48, 7-14) and the EZ Tn5$^{TH}$ (Epicentre Biotechnologies, Madison, WI) to develop a Tn5-based mutagenesis system. This system was used to generate a library of ~6,700 transposon mutants. DNA sequencing of the library was performed as previously described (Gallagher et al., 2013, mBio 4:e00604-13), yielding 2,548 unique transposon insertions and 68.5% coverage of the genome.

As a further means to modify the genome, the same hygromycin cassette was inserted into the pUCl8T-mini-Tn7T-Zeo vector and this vector was introduced via conjugation into AB5075. Tn7 insertion into the chromosome was selected for by growth on 250 μg/mL hygromycin, and confirmed by PCR across the attTn7 site on the 3' prime end of the glmS gene in the AB5075 chromosome. As proof of concept for the use of Tn7 for gene insertion in the chromosome, the lux operon was inserted into the attTn7 site. This resulted in bioluminescence of this strain, and subsequent sub-culturing of AB5075::Tn7-lux over seven days without antibiotic selection did not affect the bioluminescent signal (data not shown), suggesting that the Tn7 insertion in the chromosome is stable. Additionally, when this strain was cultured in LB broth, there was no growth defect when compared to the wild type AB5075 isolate (data not shown). These methods provide us with a means of interrupting and inserting genes on the chromosome, both of which are essential in studying bacterial pathogenesis.

In addition to the successful use of AB5075 in animal models, we were able to exploit the susceptibility of AB5075 to hygromycin to generate a Tn5 transposon insertion library and use a Tn7 transposon derivative to insert genes into the genome of this strain.

Example 2

Transposon Library Generation

As a resource for genetic analysis of AB5075, a Tn5 insertion library utilizing a tetracycline-based transposon system was generated (Gallagher et al., 2015, supra). We created an arrayed library of mutants with defined transposon insertions in most nonessential genes of the organism. Our goal was to create a colony-purified library with relatively complete genome coverage that was small enough to facilitate efficient phenotype screening. We also wanted it to include several different mutations for each gene to minimize missed genotype-phenotype associations arising from non-inactivating mutations or library cross-contamination, and to provide immediate confirmation of associations observed. To meet these objectives, we created a library made up of two to three different insertion mutants per non-essential gene. The library was created in two stages. First a large primary collection of mutants generated by random insertion mutagenesis and selection on LB agar was arrayed and sequence-defined. This collection contained an average of over ten unique insertion mutants per coding gene. Second, individual mutants from this primary collection were colony purified, re-arrayed and re-sequenced. This smaller library is made up of two to three unique, sequence-verified mutants for most genes and is called the "three-allele-library". The three mutants chosen for each gene corresponded where possible to insertions distributed between 5% and 90% of the coding sequence.

Two Tn5 transposons with different resistance markers were used to generate the mutants, with a transposon conferring tetracycline resistance (T26) accounting for the majority (95%) of the mutants in the three-allele set. Transposon T26 includes loxP sites flanking the tetracycline resistance marker, enabling excision of the marker by transient expression of Cre site-specific recombinase. For insertions in one of the six possible translational reading frames, the recombination results in an in-frame insertion of 73 codons without a stop codon, generating presumptive non-polar mutations. In addition, double mutants may be constructed by first excising the resistance marker from one mutant, then introducing a second insertion by transformation of genomic DNA from another mutant. Through iteration, strains bearing three or more mutations may also be constructed.

Three mutants were chosen with the T26 inserted into the hcp gene:
1. Item no: AB06793—
   Strain name: tnab1_kr121211p02q106
   Chromosome location: 2571476
   Direction: Forward
   *A. baumannii* locus: ABUW_2578—type VI secretion system effector, Hcp1 family
   Position within gene/total bp of gene: 450(504)
2. Item no. A806794—
   Strain name: tnab1_kr121210p03q152
   Chromosome location: 2571476
   Direction: Reverse
   *A. baumannii* locus: ABUW_2578—type VI secretion system effector, Hcp1 family
   Position within gene/total bp of gene: 450(504)

3. Item no.: AB06795—
Strain name; tnab1_kr130913p01q167
Chromosome location: 2571791
Direction: R
*A. baumannii* locus: ABUW_2578-type VI secretion system effector, Hcp1 family
Position within gene/total bp of gene: 135(504)

All three mutants had Tn5 DNA plus the tet resistance gene for selection inserted into the genome at the hcp sequence interrupting the proper translation of the protein (Gallagher et al., 2015, supra). All three were tested and mutant number three having an insertion of 135 bp was used for further study.

Example 3

Wound Model

In order to test the efficacy of a monoclonal antibody as a therapeutic antimicrobial, we sought to develop a wound infection model that utilized *A. baumannii* as a sole infectious agent and that included multiple measurable outcomes with effects that entailed quantitative end-points, which permitted small sample sizes for antimicrobial evaluation. In order to develop a new model of *A. baumannii* wound infection, three important selections were made from the outset of the study. First, female BALB/c mice were chosen, because immune responses in BALB/c mice are skewed more toward a Th2 than a Th1 response (Prabhakara et al., 2011, Infect. Immun. 79, 5010-5018; Gabaglia et al., 1999, J. Immunol. 162, 753-760), and this immune response favors the establishment of infection by the Gram-negative ESKAPE pathogens. Second, a cutaneous wound model was selected based on findings of a previous study, where an open wound did not adversely affect animal health during a >15-day protocol (Hoffman, et al., 2006, Blood 108, 3053-3060), which allowed for a large window of time to quantitatively and qualitatively measure drug efficacy in the model. Lastly, it was important that the chosen *A. baumannii* strain was virulent enough to cause an infection after a small inoculating dose. For this purpose, AB5075 was chosen for this model, as our laboratory has shown this strain is more virulent than the other *A. baumannii* isolates that were tested (Jacobs et al., 2014, supra) and, because the antibiotic susceptibilities of AB5075 were known, we could validate the model via i.p. treatment with doxycycline or rifampin. It should be noted, however, that we have evaluated other *A. baumannii* strains in this model as well (in our pilot studies). In particular, we evaluated AB5711 (Zurawski et al., 2012, J. Bacteriol. 194, 1619-1620), which was also able to cause an infection that retarded wound healing past 15 days post-inoculation (data not shown).

We developed an excisional, murine wound model in which a diminutive inoculum of a clinically relevant, multidrug-resistant *A. baumannii* isolate can proliferate, form biofilms, and be effectively treated with antibiotics (Thompson et al., 2014, Antimicrobial Agents and Chemotherapy 58, 1332-1342). The model requires a temporary, cyclophosphamide-induced neutropenia to establish an infection that can persist. A 6-mm-diameter, full-thickness wound is created in the skin overlying the thoracic spine, and after the wound bed id inoculated, it is covered with a dressing for 7 days. Uninoculated control wounds healed within 13 days, whereas infected, placebo-treated wounds remained unclosed beyond 21 days. Treated and untreated wounds are assessed with multiple quantitative and qualitative techniques that included gross pathology, weight loss and recovery, wound closure, bacterial burden, 16S rRNA community profiling, histopathology, peptide nucleic acid-fluorescence in situ hybridization, and scanning electron microscopy assessment of biofilms. The range of differences that we are able to identify with these measures in antibiotic-versus placebo-treated animals provides a clear window within which novel antimicrobial therapies can be assessed. The model can be used to evaluate antimicrobials for their ability to reduce specific pathogen loads in wounded tissues and clear biofilms. Ultimately, the mouse model approach allows for highly powered studies and serves as an initial multi-faceted in vivo assessment prior to testing in larger animals.

The retarded wound closure rate that we observed in our model using AB5075 was accompanied by a weight loss of up to 25% from the infection day body weight at 2 days postinfection (Thompson et al., 2014, Antimicrobial Agents of Chemotherapy 58, 1332-1342). Therefore, we can use weight loss as an indicator of *A. baumannii* infection in this model. Gross pathology of infected wounds indicated tissue may begin to devitalize as soon as 3 days post-infection around the wound perimeter and remain visibly swollen until 15 days after inoculation with AB5075. An evaluation of the wound using standard histopathology showed inflammation throughout the large wound perimeter that extended down to the spinal column by day 7 (data not shown). Histopathology from infected mice on day 23 revealed wounds had re-epithelialized but showed little evidence of wound perimeter contraction (data not shown). In order to investigate the dissemination of AB5075 throughout the wound bed, sections of tissue were fixed 24 hours post-infection and interrogated with *Acinetobacter*-specific PNA probes. The PNA probes revealed that the bacteria had spread rapidly beyond the wound bed through the underlying muscle and down to the spinal column (data not shown). *A. baumannii* appeared to localize in the interstitial spaces between muscle fibers and between epithelial cells (data not shown).

Regardless of the role invasion plays in vivo, the sequelae of infection that we observed postinoculation are consistent to what is observed in skin and soft tissue infections of human patients. For example, we found that *A. baumannii* penetrated the layers of tissue from the initial wound bed inoculum all the way to bone tissue (data not shown), and this was consistent with the tissue penetration observed in *A. baumannii*-infected patients (Eberle et al., 2010, Crit. Care Med. 38, 2133-2138), as well as the consideration of *A. baumannii* as a potential cause of osteomyelitis (Yun et al., 2008, J. Trauma 64, S163-S168).

To ensure the infection should be attributed to AB5075 and not to other commensals or contaminant pathogens, 16S rRNA community profiling was conducted in parallel to the CFU enumerations. Nearly all samples taken from infected but untreated wounds showed a >95% dominance of *Acinetobacter* with only a minor fraction of communities composed of *Enterobacter* in two mice from this group (data not shown). While immunosuppression is required to establish an infection and it is agreed that *A. baumannii* is a mild pathogen compared to other bacterial species, it is evident from the microbiome evaluation in this study that *A. baumannii* can establish a wound infection without other bacterial species being major contributors. In pilot studies, we also found that higher inoculums (CFU of $\geq 10^6$) resulted in sepsis and severe animal morbidity (data not shown), which also suggests that increased *A. baumannii* numbers can lead to more severe sequelae that do not require other bacterial species.

A final observation from this wound model of infection was the formation of robust biofilms within the wound bed (data not shown) and on the occlusive dressing above the wound bed (data not shown). While it is not surprising that *A. baumannii* formed biofilms in this model, given previous work showing the importance of biofilms (Brossard and Campagnari, 2012, Infect. Immun. 80, 228-233; Caddy et al, 2009, Infect. Immun. 77, 3150-3160), it was somewhat unexpected that AB5075 achieved the levels of biofilm formation observed, given that this strain does not form robust biofilms in vitro (unpublished data). Therefore, perhaps there are cues in the in vivo environment that trigger biofilm assembly, in particular with this strain, that have not been discovered. Regardless, biofilm formation in the model provides another metric for measuring antimicrobial efficacy. In fact, given that many laboratories are now developing antibiofilm strategies (Worthington, et al., 2012, Org. Biomol. Chem. 10, 7457-7474), the SEM data provided in the implementation of this model provide a qualitative assessment of an antibiofilm product.

Overall, the wound infection model we have developed uses all of the endpoints described above to provide a robust data set for evaluating infection and antimicrobials used for treatment. We believe the model will be a powerful tool to evaluate new antimicrobials for not only *A. baumannii* but also for many difficult bacterial infections caused by the MDR ESKAPE pathogens. ESKAPE pathogens include *A. baumannii, Enterococcus faecium, Staphylococcus aureus, Klebsiella pneumoniae, Pseudomonas aeruginosa* and *Enterobacter* species. The antibiotic dosing that was used herein was similar to what has been utilized in other animal models (Montero et al., 2002, Antimicrob. Agents Chemother. 46, 1946-1952, Pachon-Ibanex et al., Antimicrob. Agents Chemother. 54, 1165-1172; Rodriguez-Hernandez et al., Antimicrob. Agents Chemother. 45, 493-501) and somewhat similar to what is used clinically (Fishbain and Peleg, 2010, Clin. Infect. Dis. 51, 79-84, Holloway et al., 2006, Ann. Pharmacother. 40, 1939-1945; Wood et al., 2003, Intensive Care Med. 29, 2072-2076).

Example 4

Anti-Hcp Monoclonal Antibody 13F7

Using a bioinformatics approach we have discovered that *A. baumannii* has all the components required to have a functional T6SS. Based on sequence data from a clinical isolate AB307-0294 that causes disease in animal models (Adams et al., 2008, J. Bacteriol. 190, 8053-8064; Russo et al., 2008, Infect. Immun. 76, 3577-3586), we found that there is an insertion of about 30 kilobases (kb) of DNA sequence, which harbors a T6SS (FIG. 1). All of the genes encoding the required components (i.e. clpV, hcp, vgrG, etc.) are present in *A. baumannii* genome when compared to what is known about functional T6SS found in *Vibrio cholera (V. cholera)* and P. aerugenosa (Pukatzki et al., 2009, supra; Shrivastava and Mande, 2008, supra; Bingle et al., 2008, supra). Hcp was also present in approximately 82% of the completely sequenced *A. baumannii* and the 1000+draft genomes with a high degree of homology (99%) between each strain. These results suggest that T6SS function is conserved in almost all *A. baumannii* strains. As it turns out, pathogenic bacteria often conserve virulence mechanisms between strains and different species. We hypothesized that the T6SS components, surface proteins Hcp and VrgG required for the secretion of other T6SS effectors, are also required for full virulence in animal models of infection, would be good targets for antibody therapy.

Hcp was PCR amplified from AB5075 with restriction sites at each end (Hicp Forward NcoI—MT=55: AAAAAACCATGGCAAAAGATATATACGTT-GAGTTTCGCGG (SEQ ID NO:12) and Hcp Reverse XhoI-MT-56:AAAAAACTCGAGCGCTGCGTAAGAAGCTGT-ATTATTAG (SEQ ID NO:13). Restriction Sites—NcoI and XhoI are both non-cutters within the sequence). The full Hcp nucleic acid sequence is shown in SEQ ID N0:14, with the genomic context of the gene shown in SEQ ID NO:15, and the amino acid sequence shown in SEQ ID NO:16). Then, the gene was cloned into the pET22b vector (Novagen, Germany). After confirming a successful cloning, the protein was overexpressed in *E. coli* with the addition of IPTG. After 2 and 4 hours (hr), samples were taken to confirm expression (FIG. 2). At the 4 hr time point, the sample was lysed and purified using a nickel affinity column. The purified Hcp protein was then used to immunize mice for the generation of monoclonal antibodies.

The individual fusions from hybridoma clones were screened for binding to Hcp (antigen) and compared to original fusion screening results. Positives are highlighted in green. 13F7 was selected for all future work as it bound the tightest to the protein.

Figure 3:
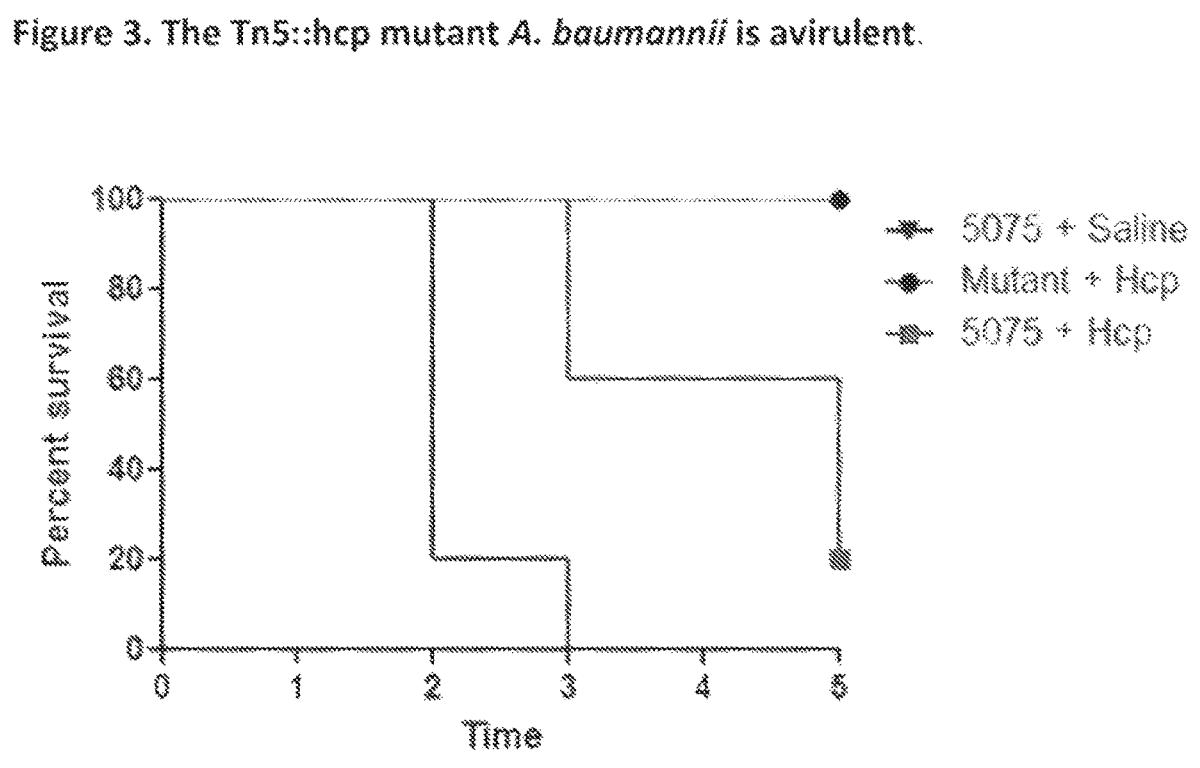

In order to test the effect of 13F7 anti-Hcp monoclonal antibody on *A. baumannii* infections, BALB/c mice received an intraperitoneal (IP) injection on Day-1, prophylactically, of 25 µg of 13F7 anti-Hcp monoclonal antibody (αHcp) diluted in sterile saline or of sterile saline alone (FIG. 3). Mice were inoculated with $5.0 \times 10^6$ colony forming units (CFU) of wild-type AB5075 or the Tn5::hcp mutant (AB06795—tnab1_kr130913p01q167) on Day 0. The data in FIG. 3 is representative of an experiment repeated twice (each group=10 mice total). The difference between the mutant and wild-type infected cells is statistically significant by log-rank (Mantel-Cox) test (P=0.0001). This data shows that: 1) the hcp mutant is attenuated in mice meaning it is avirulent. 2) That even a small dose of αHcp at 25 µg can protect mice from death via *A. baumannii* infection. In this model the pulmonary infection and sepsis at this inoculum of bacteria can cause death in three days as previously published in Jacobs et al., 2014, MBio. 5(3):01076-14.

Dose-Dependent Study of 13F7.

Mice were inoculated with $3.0 \times 10^6$ CFU of wild-type AB5075. 13F7 αHcp was given either in (a) one dose of 50 ug at day −1; (b) two doses of 50 ug at day −1 and 25 ug at day 1 for a total of 75 ug; (c) three doses of 50 ug at day −1, 25 ug at day 1, and 25 ug at day 3 for a total of 100 ug; or (d) one dose of 100 ug at day −1. Negative controls did not receive 13F7. Results (FIG. 4) indicate that 100% survival was possible with three doses totaling 100 ug, with 60% survival with two doses totaling 75 ug, and 40% survival with 1 dose of 100ug. Both the negative controls and the one dose of 50 ug showed no protection. These results suggest that the protection of the antibody is dose dependent. As the dose is increased with subsequent treatments, more protection is observed in these infected mice.

Using the murine wound model, mice were injected IP with 100 µg (Hcp (squares)) or sterile saline (circles) on Day −1. Balb/C mice were then inoculated on Day 0 with AB5075, $5.0 \times 10^6$ CFU. Wound size was measured every three days over the course of 18 days and CPU of the wound bed was measured in mice after three days. Results indicate that αHcp antibody treatment enhanced wound healing as wound size was reduced at day 6, 10, 12, and 15. Only a slight reduction in CFU was observed (about 0.5 $\log_{10}$); however, we believe the bacteria that are present are disarmed as the antibody, which binds to the amino terminus of the protein may prevent proper assembly into the functional, predicted hexamer structure.

Epitope Study

Twenty-three peptides of 15 amino acids in length of the Hcp protein were generated and adhered to an ELISA plate (Table 1). Also, as a negative control, just sterile saline was added to well 24, and as a positive control, full-length Hop protein was added to well #25. The 13F7 αHcp antibody was incubated with each peptide for one hour. Then, after extensive washing, secondary anti-mouse antibody with horseradish peroxidase (HRP) was incubated with each sample. Signal was analyzed with a spectrophotometer at $OD_{450}$ to recognize the signal. Only the amino terminus, peptide #1 (shaded), had a signal equivalent to the positive full-length protein control. Therefore, the epitope of the antibody is found in the extreme N-terminus of the protein (MKDIYVEFRGKYKVD—SEQ ID NO:9). Not to be bound by any theory, but it is likely that the monoclonal antibody, when bound to Hop at the N-terminus peptide, impedes assembly of the Hcp hexamer.

TABLE 1

| Peptide Sequences | |
| --- | --- |
| MKDIYVEFRGKYKVD | - SEQ ID NO: 9 |
| FRGKYKVDGESRDSE | - SEQ ID NO: 17 |
| DGESRDSEHKGWLEV | - SEQ ID NO: 18 |
| EHKGWLEVNSWSHN | - SEQ ID NO: 19 |
| VNSWSHNIRQPKSAT | - SEQ ID NO: 20 |
| IRQPKSATSSSVGGH | - SEQ ID NO: 21 |
| TSSSVGGHTAERVEH | - SEQ ID NO: 22 |
| HTAERVEHSDMVFVK | - SEQ ID NO: 23 |
| HSDMVFVKDLDATSP | - SEQ ID NO: 24 |
| KDLDATSPKLWEACS | - SEQ ID NO: 25 |
| PKLWEACSAGYTFDE | - SEQ ID NO: 26 |
| SAGYTEDEVQIDFYR | - SEQ ID NO: 27 |
| BVQIDFYRANGDKRI | - SBQ ID NO: 28 |

TABLE 1-continued

| Peptide Sequences | |
| --- | --- |
| RANGDKRIKYLQIKL | - SEQ ID NO: 29 |
| IKYLQIKLKHVLVSS | - SEQ ID NO: 30 |
| LKHVLVSSVTPTVNE | - SEQ ID NO: 31 |
| SVTPTVNBEGYPTEA | - SEQ ID NO: 32 |
| EEGYPTEAFGLKYAA | - SEQ ID NO: 33 |
| AFGLKYAAVEWTYNQ | - SEQ ID NO: 34 |
| AVEWTYNQQDINGTA | - SEQ ID NO: 35 |
| QQDINGTAKGVTKK | - SEQ ID NO: 36 |
| AKGAVTKKWSLSNNT | - SEQ ID NO: 37 |
| KWSLSNNTASYAA | - SEQ ID NO: 38 |

Detection of Hcp in Human Serum.

Serum was isolated from de-identified human patients that were infected with *Acinetobacter baumannii* (BR075, BR367, BR103, BR045), *Staphylococcus epidermidis* (SE610, SE339, SE1842, SE2337), or healthy, non-infected patients (HE05933, HE4176, HE7145, HE3481, HE371, HE083, HE3019, HE0821) (FIG. 7). The 13F7 αHcp antibody was used in an ELISA assay to capture Hcp protein from serum. Only patients infected with *Acinetobacter baumannii* had Hcp in their blood and serum. This suggests an αHcp antibody can be used as a diagnostic to determine if a patient has an *Acinetobacter* infection.

ELISA Capture in Biological Samples

Blood was collected from two de-identified human patients (P1 and P2) at varying times (1-4) over the course of a two week *Acinetobacter baumannii* infection (FIG. 8). Both patients received antibiotics as treatment. Patient P1 recovered, but Patient P2 did not recover, succumbed to the infection and passed away. The 13F7 αHcp antibody was used in an ELISA assay to capture Hcp protein from blood. Patient P2 signal increased over time before death, while Patient P1's signal reduced over time. This suggests that an αHcp antibody can be used as a diagnostic to predict the intensity and the potential lethality of an *Acinetobacter* infection.

What is claimed is:

1. An *Acinetobacter baumannii* strain comprising a transposon comprising an antibiotic resistance gene and two loxP sites, wherein the two loxP sites flank the antibiotic resistance gene, wherein the transposon is inserted into the genome of the *Acinetobacter baumannii* and interrupts the expression of hcp (hemolysin co-regulated protein), wherein the strain is AB5075 deposited as Patent Deposit Number PTA-127747.

2. The *Acinetobacter baumannii* strain of claim 1, wherein the transposon inserts 73 codons without a stop codon in-frame of the *Acinetobacter baumannii* genome, and interrupts the expression of hcp.

3. An immunogenic composition comprising the *Acinetobacter baumannii* strain of claim 1.

4. A method of inducing an immune response in a subject comprising administering to the subject an effective amount to induce the immune response of the *Acinetobacter baumannii* strain of claim 1.

* * * * *

SEQUENCE LISTING

```
<160> NUMBER OF SEQ ID NOS: 38

<210> SEQ ID NO 1
<211> LENGTH: 113
<212> TYPE: PRT
<213> ORGANISM: Artificial sequence
<220> FEATURE:
<223> OTHER INFORMATION: Light chain variable region of 13F7 antibody

<400> SEQUENCE: 1

Asp Ile Val Met Ala Gln Ser Pro Ser Ser Leu Asn Val Ser Ala
1               5                   10                  15

Gly Asp Lys Val Thr Met Ser Cys Lys Ser Ser Gln Ser Leu Leu
                20                  25                  30

Asn Ser Gly Asn Gln Arg Asn Tyr Leu Ala Trp Tyr Gln Gln Lys
                35                  40                  45

Pro Gly Gln Pro Pro Lys Leu Leu Ile Tyr Gly Ala Ser Thr Arg
                50                  55                  60
```

```
Glu Ser Gly Val Pro Asp Arg Phe Thr Gly Ser Gly Ser Gly Thr
             65                  70                  75

Asp Phe Thr Leu Thr Ile Ser Ser Val Gln Ala Glu Asp Leu Ala
             80                  85                  90

Val Tyr Tyr Cys Gln Asn Asp His Ile Tyr Pro Phe Thr Phe Gly
             95                 100                 105

Ser Gly Thr Lys Leu Glu Ile Lys
            110

<210> SEQ ID NO 2
<211> LENGTH: 12
<212> TYPE: PRT
<213> ORGANISM: Artificial sequence
<220> FEATURE:
<223> OTHER INFORMATION: Light chain 13F7 antibody CDR1

<400> SEQUENCE: 2

Gln Ser Leu Leu Asn Ser Gly Asn Gln Arg Asn Tyr
  1               5                  10

<210> SEQ ID NO 3
<211> LENGTH: 3
<212> TYPE: PRT
<213> ORGANISM: Artificial sequence
<220> FEATURE:
<223> OTHER INFORMATION: Light chain 13F7 antibody CDR2

<400> SEQUENCE: 3

Gly Ala Ser
  1

<210> SEQ ID NO 4
<211> LENGTH: 9
<212> TYPE: PRT
<213> ORGANISM: Artificial sequence
<220> FEATURE:
<223> OTHER INFORMATION: Light chain 13F7 antibody CDR3

<400> SEQUENCE: 4

Gln Asn Asp His Ile Tyr Pro Phe Thr
  1               5

<210> SEQ ID NO 5
<211> LENGTH: 118
<212> TYPE: PRT
<213> ORGANISM: Artificial sequence
<220> FEATURE:
<223> OTHER INFORMATION: Heavy chain variable region of 13F7 antibody

<400> SEQUENCE: 5

Glu Val Gln Leu Gln Glu Ser Gly Gly Gly Leu Val Gln Pro Gly
  1               5                  10                  15

Gly Ser Met Lys Leu Ser Cys Val Val Ser Gly Phe Ile Phe Ser
                 20                  25                  30

Ser Tyr Trp Met Ser Trp Val Arg Gln Ser Pro Glu Lys Gly Leu
                 35                  40                  45

Glu Trp Leu Ala Glu Ile Arg Leu Lys Ser Asp Asn Tyr Val Thr
                 50                  55                  60

Leu Tyr Ala Glu Ser Val Lys Gly Lys Phe Thr Ile Ser Arg Asp
             65                  70                  75

Asp Ser Lys Ser Arg Leu Phe Leu Gln Met Asn Thr Leu Arg Ala
             80                  85                  90
```

Glu Asp Thr Gly Ile Tyr Tyr Cys Thr Arg Ser Tyr His Ala Leu
            95                 100                 105

Asp Tyr Trp Gly Gln Gly Thr Ser Val Thr Val Ser Ser
            110                 115

<210> SEQ ID NO 6
<211> LENGTH: 8
<212> TYPE: PRT
<213> ORGANISM: Artificial sequence
<220> FEATURE:
<223> OTHER INFORMATION: Heavy chain 13F7 antibody CDR1

<400> SEQUENCE: 6

Gly Phe Ile Phe Ser Ser Tyr Trp
 1               5

<210> SEQ ID NO 7
<211> LENGTH: 10
<212> TYPE: PRT
<213> ORGANISM: Artificial sequence
<220> FEATURE:
<223> OTHER INFORMATION: Heavy chain 13F7 antibody CDR2

<400> SEQUENCE: 7

Ile Arg Leu Lys Ser Asp Asn Tyr Val Thr
 1               5                  10

<210> SEQ ID NO 8
<211> LENGTH: 8
<212> TYPE: PRT
<213> ORGANISM: Artificial sequence
<220> FEATURE:
<223> OTHER INFORMATION: Heavy chain 13F7 antibody CDR3

<400> SEQUENCE: 8

Arg Ser Tyr His Ala Leu Asp Tyr
 1               5

<210> SEQ ID NO 9
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 9

Met Lys Asp Ile Tyr Val Glu Phe Arg Gly Lys Tyr Lys Val Asp
 1               5                  10                  15

<210> SEQ ID NO 10
<211> LENGTH: 354
<212> TYPE: DNA
<213> ORGANISM: Artificial sequence
<220> FEATURE:
<223> OTHER INFORMATION: Heavy chain variable region 13F7 antibody

<400> SEQUENCE: 10
gaggtgcagc tgcaggagtc tggaggaggc ttggtgcaac ctggaggatc         50
catgaaactc tcctgtgtag tctctggatt tattttcagt agttactgga        100
tgtcttgggt ccgccagtct ccagagaagg ggcttgagtg gcttgctgaa        150
attagattga atctgataa ttatgtaaca ctttatgcgg agtctgttaa         200
agggaagttc accatctcaa gagatgattc caaaagtcgt ctctttctgc        250

| | |
|---|---|
| aaatgaatac cttaagagct gaagacactg gaatttatta ctgtacgagg | 300 |
| agttaccatg ctttggacta ctggggtcaa ggaacctcag tcaccgtctc | 350 |
| ctca | 354 |

<210> SEQ ID NO 11
<211> LENGTH: 338
<212> TYPE: DNA
<213> ORGANISM: Artificial sequence
<220> FEATURE:
<223> OTHER INFORMATION: Light chain variable region 13F7 antibody

<400> SEQUENCE: 11

| | |
|---|---|
| gacattgtga tggcacagtc tccttcctcc ctgaatgtgt cagcaggaga | 50 |
| caaggtcact atgagctgca agtccagtca gagtctgttg aacagtggaa | 100 |
| atcagaggaa ctacttggcc tggtaccaac agaaaccagg gcagcctcct | 150 |
| aaactgttga tctacggggc ttccactagg aatctggggg tccctgatcg | 200 |
| cttcacaggc agtggatctg gaaccgattt cactcttacc atcagcagtg | 250 |
| tgcaggctga agacctggca gtttattact gtcagaatga tcatatttat | 300 |
| ccattcacgt tcggctcggg acaaagctgg aaataaaa | 338 |

<210> SEQ ID NO 12
<211> LENGTH: 40
<212> TYPE: DNA
<213> ORGANISM: Artificial sequence
<220> FEATURE:
<223> OTHER INFORMATION: Hcp Forward NcoI-MT=55 primer

<400> SEQUENCE: 12

| | |
|---|---|
| aaaaaaccat ggcaaaagat atatacgttg agtttcgcgg | 40 |

<210> SEQ ID NO 13
<211> LENGTH: 38
<212> TYPE: DNA
<213> ORGANISM: Artificial sequence
<220> FEATURE:
<223> OTHER INFORMATION: Hcp Reverse XhoI MT=56 primer

<400> SEQUENCE: 13

| | |
|---|---|
| aaaaaactcg agcgctgcgt aagaagctgt attattag | 38 |

<210> SEQ ID NO 14
<211> LENGTH: 504
<212> TYPE: DNA
<213> ORGANISM: Acinetobacter baumannii
<220> FEATURE:
<223> OTHER INFORMATION: Hcp

<400> SEQUENCE: 14

| | |
|---|---|
| atgaaagata tatacgttga gtttcgcggt aaatataaag ttgatggaga | 50 |
| gtctcgtgat tctgagcaca aaggttggtt agaagttaac tcttggtctc | 100 |
| ataacatccg tcaacctaaa tctgctactt caagtagtgt gggcggccac | 150 |
| actgctgaac gtgttgaaca ttctgacatg gttttcgtga agacttaga | 200 |
| cgcaactagc cctaaattat gggaagcttg ttcagctggt tatacatttg | 250 |
| atgaagtaca aatcgacttc tatcgcgcaa atggcgataa acgtatcaag | 300 |
| tacttacaaa tcaaattgaa gcacgtttta gtttctagtg tgactccaac | 350 |
| tgttaacgaa gaaggcgttc ctacagaagc attcggtttg aaatatgctg | 400 |

-continued

| | |
|---|---|
| ctgttgagtg gacttataac caacaagata ttaacggtac tgctaaaggt | 450 |
| gctgttacta agaaatggtc actttctaat aatacagctt cttacgcagc | 500 |
| gtaa | 504 |

<210> SEQ ID NO 15
<211> LENGTH: 4504
<212> TYPE: DNA
<213> ORGANISM: Acinetobacter baumannii
<220> FEATURE:
<223> OTHER INFORMATION: Genomic context of Hcp gene

<400> SEQUENCE: 15

| | |
|---|---|
| gaagcttcag cgaattcgac ctccacgtgt tcagcttaca tatgatgtcg | 50 |
| aaattggtga tgcgaaagaa gcgaaagaac taccattcgt tgtaggtgta | 100 |
| atgggtgatt tttcagctgc atctgagctt gagcgtacaa aattaaaaga | 150 |
| taaaaaattc attaatgtcg atttagtaaa tattgatgaa gtaatggaat | 200 |
| ctctgtctcc aagagctgct tttcaagtag acaatacgtt gacagaagaa | 250 |
| ggcggtaaaa tggctgttga tttaacgttt aagtcaatgg aagattttcg | 300 |
| cccggaaaat gttgtacagc aagttgatcc attaaagaaa ttggttgagg | 350 |
| cgcgtgagcg tttaaccgat ttaagaaaca aaatttcaaa cagtgagcgt | 400 |
| ttagaagacc tgcttgatga ggttcttaaa aatactgatc aaatccgtaa | 450 |
| attaagtgcg gaggccgatc atgaataata ctcaatcagc agcaatgcca | 500 |
| cttgttgaaa atgaagaagt taatcttttg gattcgattg ttgaacaaag | 550 |
| ccgtattgca cgaaatgaag aagaacattc tcgtgctaaa agcttaattg | 600 |
| gtgagctcgc taagaagta atggcaggga ccattactgt ttctgaaaat | 650 |
| atgactttat caatcgataa gcgtattgca gaaattgatg ctctgatttc | 700 |
| aaagcagtta agtcagatca tgcacaatga acaattccaa aaaattgagt | 750 |
| caacttggcg tggtctttat tacttttgtc aggaaacgcc ttcaaatccg | 800 |
| ctcattaaaa ttcgtatgct caatacgact aagaaagagt tggtaaaaga | 850 |
| tttccaaggt gctacagact tgatcaaag cactttgttt aagaaaatct | 900 |
| acgaagaaga atacggttct tttggtggtg caccatactc agcattaatt | 950 |
| ggtgattttg agtttgaccg tactccatct gatatgtatt tgcttgagca | 1000 |
| aatctctcat gttgcagcgg cagcacatgc acccttat tcagctgcta | 1050 |
| gtccgagcat tttaggcctt gaatcattta cagatattga tcgtcctaga | 1100 |
| gatgtttcaa aaatctttga aaccgctgaa atatgttcaat ggcgttcgtt | 1150 |
| ccgtgatagt gaagactccc gttatgttgc attgactttg cctcatgtct | 1200 |
| tgggtcgtct cccatatcat ccaaaagaag gtactgcgac agaaggcttt | 1250 |
| aatttttattg aagatgtttc tggtgaaaac cacaatgaat atttgtggat | 1300 |
| gaatgcagct tatgcttttg gtactcgctt aacaaatgca tttgatatgc | 1350 |
| atggttggtg tgctgctatt cgcggtgttg aaggtggtgg tttagttgaa | 1400 |
| ggcttgccag tacatacttt taaaacacaa gatggcgaag tggtattcaa | 1450 |
| gtgtccaact gaaattgcaa tcacggatcg ccgtgaaaaa gagttaagcg | 1500 |
| atctaggttt cattccgtta gtacattgta aaaatacaga ttacgcagct | 1550 |

-continued

```
ttctttggcg cgcaatcaac tcaaaaacct aaaaaatatg acaatgatac    1600
agccaatgca aactcggctt tatcaagtca gattcagtac atcatggctg    1650
tttcacgtat tgcacattac ttaaaagcaa tgatgcgaga taaagtgggt    1700
agctttgctt ctgctggaaa tgttgaagca ttcttaaatg agtggttgtc    1750
acagtatgtc ttacttgacg atggtgcttc tcaagaagca aaagctcaat    1800
acccgttacg tgaagcgtct gtaaaagttg tagaagatcc tgctcaacca    1850
ggtcactaca aatctgtggt tttcttgcga ccacatttcc agctggatga    1900
gttgtcggtt tctttacgac ttgtcactga gttacctcag tcctcaaatt    1950
aatcaaggtc agctaaagaa taactttaaa ttaaaatagg aaagttctaa    2000
atgaaagata tatacgttga gtttcgcggt aaatataaag ttgatggaga    2050
gtctcgtgat tctgagcaca aaggttggtt agaagttaac tcttggtctc    2100
ataacatccg tcaacctaaa tctgctactt caagtagtgt gggcggccac    2150
actgctgaac gtgttgaaca ttctgacatg gttttcgtga aagacttaga    2200
cgcaactagc cctaaattat gggaagcttg ttcagctggt tatacatttg    2250
atgaagtaca aatcgacttc tatcgcgcaa atggcgataa acgtatcaag    2300
tacttacaaa tcaaattgaa gcacgtttta gtttctagtg tgactccaac    2350
tgttaacgaa gaaggcgttc ctacagaagc attcggtttg aaatatgctg    2400
ctgttgagtg gacttataac caacaagata ttaacggtac tgctaaaggt    2450
gctgttacta gaaatggtc actttctaat aatacagctt cttacgcagc    2500
gtaattattt aagtgaatat ttggtggagg ctgacataaa gttagcctct    2550
gctgtcttta aatatacttt gttgtgaact cgaatgaact tagatcggct    2600
ttatccatac ggatttcgtt caactttatt tgatcgctta attccagaaa    2650
gtgaagatta tgcaaaaggt cttttctattc agcaattaag agaatctgta    2700
gcaaaggatt tagaagattt gctcaatagt cgggtagcaa agttagatca    2750
tgtgattgat gactatccac ttgtaaaaaa atcgatactt cagttcggga    2800
ttattgattt tgtggggctt tctacagcca accctctgga tcgggataaa    2850
atttgccaat ccattgagca atcaatagca gctcatgaac ctcggctaag    2900
acaaatacgg gtagagatgt tattagatgg acataatatg ggcgcattat    2950
gtttaagtat tcaggcttat ctaaatattc acccttata tgaacctgtt    3000
gtatttgatg cattgttaaa accaacaacg cagcaatatg taatttcagc    3050
aagaacttaa gcgtagtggg tgtgttgtga tagaagagct tttaccgttt    3100
tatgaaaaac aattacaaga atttggtcaa caatctcggg aatttgccca    3150
aaaatatcca aaaattgctc agcgcttatc tttaaatcaa gagcaaattg    3200
atgacccaca tattgaacgt ctgattcagg cttttttcgct gattgctgct    3250
cgaattgata aaaaactaac agacagttac gatgttttta ctcgttcttt    3300
atttgaggtg atgttccctc aatacttacg acattttcct gcgtgttcag    3350
ttgttagttt tgaagatatt aataagatta aacagcttac agaacctcat    3400
ctcgtacctc accatacggt tttgaaatct cgtagtttca aagggtgca    3450
gtgtgagttt aatacaactc aagatgttaa attactacct attcatttaa    3500
gtggtttaga ttttaaaact acacctagtg cacatatgca cttaaatcaa    3550
```

-continued

```
aatgcgacgt tgagccttaa atttgaaatt tttaataatg ctcatgcttg      3600
tttaactgat gagaagcttc ctatttattt ggatgctatc tctaatttc       3650 ctctacaggt ccttgatagt attttcaaaa aaggaaccag ttttgcggtt      3700
aaatatggac aaacaattgt agaattgagc aagaatccat tcgaattgat      3750
tggttttgca gaacaagaaa gtttattacc gcttgatcaa catacccatc      3800
atgcttatcg tttgttgatg gaatacttt gtttcccgga aaagtttagt       3850
tatcttaagc tcgatttaga ttttttaaag cgaatacctc agcatgtatc      3900
cgaacttgag cttttaattc atttcaaatt aaacttaaat gatcaagccg      3950
ttgttagaaa ctattctgag ctaaatattg caaactttaa attatttact      4000
accccagtaa ttaatttatt tgaaaaatat gctgaacccc agaagatagt      4050
tcataagcaa ttagaatatc ctttagttac agatgcacat catcctgagt      4100
tttatcaggt atattcaata cttgagatga atatggtgcg tgaaaaaaca      4150
aatcaagaag aaagctatgt tcctgttttg ccttttttg cgatgagcca       4200 ttaccacaat gatacagctc gcttttttta ctcagtaaac tatcaaaagt      4250
tacagtccaa tttcgttgaa atgggctatt ccattatttc taaaaattta     4300 aatccattt caacgcgctc agattttatt agcaccaaat tattatgttc       4350
aaaccgtgat ttacctcatg aagcactggg tcagtctaat aacgtattaa      4400
atttaaatga tagtagcttg gcgagacgtg ccattgtttt aaaacgacct      4450
accaagcctt ataagtttga acaaggccaa agtgaacagt ggcgtgtgat      4500
ctcg                                                       4504
```

<210> SEQ ID NO 16
<211> LENGTH: 167
<212> TYPE: PRT
<213> ORGANISM: Artificial sequence
<220> FEATURE:
<223> OTHER INFORMATION: Hcp polypeptide

<400> SEQUENCE: 16

```
Met Lys Asp Ile Tyr Val Glu Phe Arg Gly Lys Tyr Lys Val Asp
  1               5                  10                  15

Gly Glu Ser Arg Asp Ser Glu His Lys Gly Trp Leu Glu Val Asn
                 20                  25                  30

Ser Trp Ser His Asn Ile Arg Gln Pro Lys Ser Ala Thr Ser Ser
                 35                  40                  45

Ser Val Gly Gly His Thr Ala Glu Arg Val Glu His Ser Asp Met
                 50                  55                  60

Val Phe Val Lys Asp Leu Asp Ala Thr Ser Pro Lys Leu Trp Glu
                 65                  70                  75

Ala Cys Ser Ala Gly Tyr Thr Phe Asp Glu Val Gln Ile Asp Phe
                 80                  85                  90

Tyr Arg Ala Asn Gly Asp Lys Arg Ile Lys Tyr Leu Gln Ile Lys
                 95                 100                 105

Leu Lys His Val Leu Val Ser Ser Val Thr Pro Thr Val Asn Glu
                110                 115                 120

Glu Gly Val Pro Thr Glu Ala Phe Gly Leu Lys Tyr Ala Ala Val
                125                 130                 135

Glu Trp Thr Tyr Asn Gln Gln Asp Ile Asn Gly Thr Ala Lys Gly
```

```
                      140                 145                 150
Ala Val Thr Lys Lys Trp Ser Leu Ser Asn Asn Thr Ala Ser Tyr
              155                 160                 165

Ala  Ala

<210> SEQ ID NO 17
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 17

Phe Arg Gly Lys Tyr Lys Val Asp Gly Glu Ser Arg Asp Ser Glu
 1               5                  10                  15

<210> SEQ ID NO 18
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 18

Asp Gly Glu Ser Arg Asp Ser Glu His Lys Gly Trp Leu Glu Val
 1               5                  10                  15

<210> SEQ ID NO 19
<211> LENGTH: 14
<212> TYPE: PRT
<213> ORGANISM: Artificial sequence
<220> FEATURE:
<223> OTHER INFORMATION: Hcp peptide epitope

<400> SEQUENCE: 19

Glu His Lys Gly Trp Leu Glu Val Asn Ser Trp Ser His Asn
 1               5                  10

<210> SEQ ID NO 20
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 20

Val Asn Ser Trp Ser His Asn Ile Arg Gln Pro Lys Ser Ala Thr
 1               5                  10                  15

<210> SEQ ID NO 21
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 21

Ile Arg Gln Pro Lys Ser Ala Thr Ser Ser Ser Val Gly Gly His
 1               5                  10                  15

<210> SEQ ID NO 22
<211> LENGTH: 15
<212> TYPE: PRT
<213> ORGANISM: Artificial sequence
<220> FEATURE:
<223> OTHER INFORMATION: Hcp peptide epitope
```

<400> SEQUENCE: 22

Thr Ser Ser Ser Val Gly Gly His Thr Ala Glu Arg Val Glu His
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 23

His Thr Ala Glu Arg Val Glu His Ser Asp Met Val Phe Val Lys
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 24

His Ser Asp Met Val Phe Val Lys Asp Leu Asp Ala Thr Ser Pro
1               5                   10                  15

<210> SEQ ID NO 25
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 25

Lys Asp Leu Asp Ala Thr Ser Pro Lys Leu Trp Glu Ala Cys Ser
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 26

Pro Lys Leu Trp Glu Ala Cys Ser Ala Gly Tyr Thr Phe Asp Glu
1               5                   10                  15

<210> SEQ ID NO 27
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 27

Ser Ala Gly Tyr Thr Phe Asp Glu Val Gln Ile Asp Phe Tyr Arg
1               5                   10                  15

<210> SEQ ID NO 28
<211> LENGTH: 15
<212> TYPE: PRT
<213> ORGANISM: Artificial sequence
<220> FEATURE:
<223> OTHER INFORMATION: Hcp peptide epitope

```
<400> SEQUENCE: 28

Glu Val Gln Ile Asp Phe Tyr Arg Ala Asn Gly Asp Lys Arg Ile
  1               5                  10                  15

<210> SEQ ID NO 29
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 29

Arg Ala Asn Gly Asp Lys Arg Ile Lys Tyr Leu Gln Ile Lys Leu
  1               5                  10                  15

<210> SEQ ID NO 30
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 30

Ile Lys Tyr Leu Gln Ile Lys Leu Lys His Val Leu Val Ser Ser
  1               5                  10                  15

<210> SEQ ID NO 31
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 31

Leu Lys His Val Leu Val Ser Ser Val Thr Pro Thr Val Asn Glu
  1               5                  10                  15

<210> SEQ ID NO 32
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 32

Ser Val Thr Pro Thr Val Asn Glu Glu Gly Val Pro Thr Glu Ala
  1               5                  10                  15

<210> SEQ ID NO 33
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 33

Glu Glu Gly Val Pro Thr Glu Ala Phe Gly Leu Lys Tyr Ala Ala
  1               5                  10                  15

<210> SEQ ID NO 34
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 34
```

-continued

```
Ala Phe Gly Leu Lys Tyr Ala Ala Val Glu Trp Thr Tyr Asn Gln
  1               5                  10                  15

<210> SEQ ID NO 35
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 35

Ala Val Glu Trp Thr Tyr Asn Gln Gln Asp Ile Asn Gly Thr Ala
  1               5                  10                  15

<210> SEQ ID NO 36
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 36

Gln Gln Asp Ile Asn Gly Thr Ala Lys Gly Ala Val Thr Lys Lys
  1               5                  10                  15

<210> SEQ ID NO 37
<211> LENGTH: 15
<212> TYPE: PRT
<213> ORGANISM: Artificial sequence
<220> FEATURE:
<223> OTHER INFORMATION: Hcp peptide epitope

<400> SEQUENCE: 37

Ala Lys Gly Ala Val Thr Lys Lys Trp Ser Leu Ser Asn Asn Thr
  1               5                  10                  15

<210> SEQ ID NO 38
<211> LENGTH: 13
<212> TYPE: PRT
<213> ORGANISM: Artificial sequence
<220> FEATURE:
<223> OTHER INFORMATION: Hcp peptide epitope

<400> SEQUENCE: 38

Lys Trp Ser Leu Ser Asn Asn Thr Ala Ser Tyr Ala Ala
  1               5                  10
```